US011628571B2

(12) United States Patent
Pinter et al.

(10) Patent No.: US 11,628,571 B2
(45) Date of Patent: *Apr. 18, 2023

(54) SOCIAL BEHAVIOR RULES FOR A MEDICAL TELEPRESENCE ROBOT

(71) Applicants: InTouch Technologies, Inc., Santa Barbara, CA (US); iRobot Corporation, Bedford, MA (US)

(72) Inventors: Marco Pinter, Goleta, CA (US); Fuji Lai, Goleta, CA (US); Daniel Steven Sanchez, Summerland, CA (US); James Ballantyne, Santa Barbara, CA (US); David Bjorn Roe, Santa Barbara, CA (US); Yulun Wang, Goleta, CA (US); Charles S. Jordan, Santa Barbara, CA (US); Orjeta Taka, Peabody, MA (US); Cheuk Wah Wong, Concord, MA (US)

(73) Assignees: TELADOC HEALTH, INC., Purchase, NY (US); IROBOT CORPORATION, Bedford, MA (US)

( * ) Notice: Subject to any disclaimer, the term of this patent is extended or adjusted under 35 U.S.C. 154(b) by 162 days.

This patent is subject to a terminal disclaimer.

(21) Appl. No.: 17/027,335

(22) Filed: Sep. 21, 2020

(65) Prior Publication Data

US 2021/0008722 A1 Jan. 14, 2021

Related U.S. Application Data

(63) Continuation of application No. 16/418,605, filed on May 21, 2019, now Pat. No. 10,780,582, which is a
(Continued)

(51) Int. Cl.
*B25J 9/16* (2006.01)
*G06Q 50/22* (2018.01)
*G16H 40/67* (2018.01)

(52) U.S. Cl.
CPC ............ *B25J 9/1676* (2013.01); *G06Q 50/22* (2013.01); *G16H 40/67* (2018.01); *Y10S 901/01* (2013.01); *Y10S 901/47* (2013.01); *Y10S 901/49* (2013.01)

(58) Field of Classification Search
USPC .................................................. 700/245–264
See application file for complete search history.

(56) References Cited

U.S. PATENT DOCUMENTS

| 3,821,995 A | 7/1974 | Aghnides |
| 4,107,689 A | 8/1978 | Jellinek |

(Continued)

FOREIGN PATENT DOCUMENTS

| AU | 1216200 | 5/2000 |
| CA | 2289697 | 11/1998 |

(Continued)

OTHER PUBLICATIONS

"Google Translation of Innovations Report," From research project to television star: Care-O-bot in ZDF series, available online at http://www._innovations-report.de/specials/printa.php?id=5157, Sep. 28, 2001, 2 pages.

(Continued)

*Primary Examiner* — Jonathan L Sample
(74) *Attorney, Agent, or Firm* — Kory D. Christensen

(57) ABSTRACT

Devices, systems, and methods for social behavior of a telepresence robot are disclosed herein. A telepresence robot may include a drive system, a control system, an object detection system, and a social behaviors component. The drive system is configured to move the telepresence robot. The control system is configured to control the drive system to drive the telepresence robot around a work area. The object detection system is configured to detect a human in proximity to the telepresence robot. The social behaviors
(Continued)

component is configured to provide instructions to the control system to cause the telepresence robot to operate according to a first set of rules when a presence of one or more humans is not detected and operate according to a second set of rules when the presence of one or more humans is detected.

15 Claims, 12 Drawing Sheets

Related U.S. Application Data continuation of application No. 15/720,214, filed on Sep. 29, 2017, now Pat. No. 10,328,576, which is a continuation of application No. 14/931,641, filed on Nov. 3, 2015, now Pat. No. 9,776,327, which is a continuation of application No. 14/550,743, filed on Nov. 21, 2014, now Pat. No. 9,174,342, which is a continuation of application No. PCT/US2013/031778, filed on Mar. 14, 2013.

(60) Provisional application No. 61/766,623, filed on Feb. 19, 2013, provisional application No. 61/674,796, filed on Jul. 23, 2012, provisional application No. 61/674,794, filed on Jul. 23, 2012, provisional application No. 61/674,782, filed on Jul. 23, 2012, provisional application No. 61/650,205, filed on May 22, 2012.

(56) References Cited

U.S. PATENT DOCUMENTS

| | | | |
|---|---|---|---|
| 4,213,182 A | 7/1980 | Eichelberger et al. | |
| 4,413,693 A | 11/1983 | Derby | |
| 4,471,354 A | 9/1984 | Smith | |
| 4,519,466 A | 5/1985 | Shiraishi | |
| 4,553,309 A | 11/1985 | Hess et al. | |
| 4,572,594 A | 2/1986 | Schwartz | |
| 4,625,274 A | 11/1986 | Schroeder | |
| 4,638,445 A * | 1/1987 | Mattaboni | B25J 9/0003 |
| | | | 706/904 |
| 4,652,204 A | 3/1987 | Arnett | |
| 4,669,168 A | 6/1987 | Tamura et al. | |
| 4,679,152 A | 7/1987 | Perdue | |
| 4,697,278 A | 9/1987 | Fleischer | |
| 4,697,472 A | 10/1987 | Hiyane | |
| 4,709,265 A | 11/1987 | Silverman et al. | |
| 4,733,737 A | 3/1988 | Falamak | |
| 4,751,658 A | 6/1988 | Kadonoff et al. | |
| 4,766,581 A | 8/1988 | Korn et al. | |
| 4,777,416 A | 10/1988 | George et al. | |
| 4,797,557 A | 1/1989 | Ohman | |
| 4,803,625 A | 2/1989 | Fu et al. | |
| 4,847,764 A | 7/1989 | Halvorson | |
| 4,875,172 A | 10/1989 | Kanayama | |
| 4,878,501 A | 11/1989 | Shue | |
| 4,942,512 A | 7/1990 | Kohno | |
| 4,942,538 A | 7/1990 | Yuan et al. | |
| 4,953,159 A | 8/1990 | Hayden et al. | |
| 4,974,607 A | 12/1990 | Miwa | |
| 4,977,971 A | 12/1990 | Crane et al. | |
| 5,006,988 A | 4/1991 | Borenstein et al. | |
| 5,040,116 A | 8/1991 | Evans et al. | |
| 5,051,906 A | 9/1991 | Evans et al. | |
| 5,073,749 A | 12/1991 | Kanayama | |
| 5,084,828 A | 1/1992 | Kaufman et al. | |
| 5,130,794 A | 7/1992 | Ritchey | |
| 5,148,591 A | 9/1992 | Pryor | |
| 5,153,833 A | 10/1992 | Gordon et al. | |
| 5,155,684 A | 10/1992 | Burke et al. | |
| 5,157,491 A | 10/1992 | Kassatly | |
| 5,182,641 A | 1/1993 | Diner et al. | |
| 5,186,270 A | 2/1993 | West | |
| 5,193,143 A | 3/1993 | Kaemmerer et al. | |
| 5,217,453 A | 6/1993 | Wilk | |
| 5,220,263 A | 6/1993 | Onishi et al. | |
| 5,224,157 A | 6/1993 | Yamada et al. | |
| 5,230,023 A | 7/1993 | Nakano | |
| 5,231,693 A | 7/1993 | Backes et al. | |
| 5,236,432 A | 8/1993 | Matsen et al. | |
| 5,262,944 A | 11/1993 | Weisner et al. | |
| 5,305,427 A | 4/1994 | Nagata | |
| 5,315,287 A | 5/1994 | Sol | |
| 5,319,611 A | 6/1994 | Korba | |
| 5,341,242 A | 8/1994 | Gilboa et al. | |
| 5,341,459 A | 8/1994 | Backes | |
| 5,341,854 A | 8/1994 | Zezulka et al. | |
| 5,347,306 A | 9/1994 | Nitta | |
| 5,347,457 A | 9/1994 | Tanaka et al. | |
| 5,350,033 A | 9/1994 | Kraft | |
| 5,366,896 A | 11/1994 | Margrey et al. | |
| 5,374,879 A | 12/1994 | Pin et al. | |
| 5,375,195 A | 12/1994 | Johnson | |
| 5,400,068 A | 3/1995 | Ishida et al. | |
| 5,417,210 A | 5/1995 | Funda et al. | |
| 5,419,008 A | 5/1995 | West | |
| 5,436,542 A | 7/1995 | Petelin et al. | |
| 5,441,042 A | 8/1995 | Putman | |
| 5,441,047 A | 8/1995 | David et al. | |
| 5,442,728 A | 8/1995 | Kaufman et al. | |
| 5,462,051 A | 10/1995 | Oka et al. | |
| 5,486,853 A | 1/1996 | Baxter et al. | |
| 5,510,832 A | 4/1996 | Garcia | |
| 5,511,147 A | 4/1996 | Abdel-Malek | |
| 5,528,289 A | 6/1996 | Cortjens et al. | |
| 5,539,741 A | 7/1996 | Barraclough et al. | |
| 5,544,649 A | 8/1996 | David et al. | |
| 5,550,577 A | 8/1996 | Verbiest et al. | |
| 5,553,609 A | 9/1996 | Chen et al. | |
| 5,563,998 A | 10/1996 | Yaksich et al. | |
| 5,572,229 A | 11/1996 | Fischer | |
| 5,572,999 A | 11/1996 | Funda et al. | |
| 5,594,859 A | 1/1997 | Palmer et al. | |
| 5,598,208 A | 1/1997 | McClintock | |
| 5,600,573 A | 2/1997 | Hendricks et al. | |
| 5,617,539 A | 4/1997 | Ludwig et al. | |
| 5,619,341 A | 4/1997 | Auyeung et al. | |
| 5,623,679 A | 4/1997 | Rivette et al. | |
| 5,630,566 A | 5/1997 | Case | |
| 5,636,218 A | 6/1997 | Ishikawa et al. | |
| 5,652,849 A | 7/1997 | Conway et al. | |
| 5,657,246 A | 8/1997 | Hogan et al. | |
| 5,659,779 A | 8/1997 | Laird et al. | |
| 5,673,082 A | 9/1997 | Wells et al. | |
| 5,675,229 A | 10/1997 | Thorne | |
| 5,682,199 A | 10/1997 | Lankford | |
| 5,684,695 A | 11/1997 | Bauer | |
| 5,701,904 A | 12/1997 | Simmons et al. | |
| 5,734,804 A | 3/1998 | Bergner | |
| 5,734,805 A | 3/1998 | Isensee et al. | |
| 5,739,657 A | 4/1998 | Takayama et al. | |
| 5,748,629 A | 5/1998 | Caldara et al. | |
| 5,749,058 A | 5/1998 | Hashimoto | |
| 5,749,362 A | 5/1998 | Funda et al. | |
| 5,754,631 A | 5/1998 | Cave | |
| 5,758,079 A | 5/1998 | Ludwig et al. | |
| 5,762,458 A | 6/1998 | Wang et al. | |
| 5,764,731 A | 6/1998 | Yablon | |
| 5,767,897 A | 6/1998 | Howell | |
| 5,786,846 A | 7/1998 | Hiroaki | |
| 5,787,545 A | 8/1998 | Colens | |
| 5,787,745 A | 8/1998 | Colens | |
| 5,793,365 A | 8/1998 | Tang et al. | |
| 5,801,755 A | 9/1998 | Echerer | |
| 5,802,494 A | 9/1998 | Kuno | |
| 5,836,872 A | 11/1998 | Kenet et al. | |
| 5,838,575 A | 11/1998 | Lion | |
| 5,844,599 A | 12/1998 | Hildin | |
| 5,857,534 A | 1/1999 | Devault et al. | |
| 5,867,494 A | 2/1999 | Krishnaswamy et al. | |
| 5,867,653 A | 2/1999 | Aras et al. | |

(56) References Cited

U.S. PATENT DOCUMENTS

| | | |
|---|---|---|
| 5,871,451 A | 2/1999 | Unger et al. |
| 5,872,922 A | 2/1999 | Hogan et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober |
| 5,954,692 A | 9/1999 | Smith et al. |
| 5,959,423 A | 9/1999 | Nakanishi et al. |
| 5,961,446 A | 10/1999 | Beller et al. |
| 5,966,130 A | 10/1999 | Benman |
| 5,973,724 A | 10/1999 | Riddle |
| 5,974,446 A | 10/1999 | Sonnenreich et al. |
| 5,983,263 A | 11/1999 | Rothrock et al. |
| 5,995,119 A | 11/1999 | Cosatto et al. |
| 5,995,884 A | 11/1999 | Allen et al. |
| 5,999,977 A | 12/1999 | Riddle |
| 6,006,140 A | 12/1999 | Carter |
| 6,006,946 A | 12/1999 | Williams et al. |
| 6,031,845 A | 2/2000 | Walding |
| 6,036,812 A | 3/2000 | Williams et al. |
| 6,047,259 A | 4/2000 | Campbell et al. |
| 6,091,219 A | 7/2000 | Maruo et al. |
| 6,113,343 A | 9/2000 | Goldenberg et al. |
| 6,133,944 A | 10/2000 | Braun et al. |
| 6,135,228 A | 10/2000 | Asada et al. |
| 6,148,100 A | 11/2000 | Anderson et al. |
| 6,160,582 A | 12/2000 | Hill |
| 6,170,929 B1 | 1/2001 | Wilson et al. |
| 6,175,779 B1 | 1/2001 | Barrett |
| 6,189,034 B1 | 2/2001 | Riddle |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba et al. |
| 6,233,504 B1 | 5/2001 | Das et al. |
| 6,233,735 B1 | 5/2001 | Ebihara |
| 6,250,928 B1 | 6/2001 | Poggio et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,292,714 B1 | 9/2001 | Okabayashi |
| 6,304,050 B1 | 10/2001 | Skaar et al. |
| 6,314,631 B1 | 11/2001 | Pryor |
| 6,317,652 B1 * | 11/2001 | Osada ............... B25J 19/023 901/1 |
| 6,317,953 B1 | 11/2001 | Pryor |
| 6,321,137 B1 | 11/2001 | De Smet |
| 6,324,184 B1 | 11/2001 | Hou et al. |
| 6,324,443 B1 | 11/2001 | Kurakake et al. |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,342,915 B1 | 1/2002 | Ozaki et al. |
| 6,346,950 B1 | 2/2002 | Jouppi |
| 6,346,962 B1 | 2/2002 | Goodridge |
| 6,369,847 B1 | 4/2002 | James et al. |
| 6,373,855 B1 | 4/2002 | Downing et al. |
| 6,381,515 B1 | 4/2002 | Inoue et al. |
| 6,389,329 B1 | 5/2002 | Colens |
| 6,400,378 B1 | 6/2002 | Snook |
| 6,408,230 B2 | 6/2002 | Wada |
| 6,411,055 B1 | 6/2002 | Fujita et al. |
| 6,430,471 B1 | 8/2002 | Kintou et al. |
| 6,430,475 B2 | 8/2002 | Okamoto et al. |
| 6,438,457 B1 | 8/2002 | Kokoo et al. |
| 6,445,964 B1 | 9/2002 | White et al. |
| 6,449,762 B1 | 9/2002 | Mcelvain |
| 6,452,915 B1 | 9/2002 | Jorgensen |
| 6,457,043 B1 | 9/2002 | Kwak et al. |
| 6,459,955 B1 | 10/2002 | Bartsch et al. |
| 6,463,352 B1 | 10/2002 | Tadokoro et al. |
| 6,463,361 B1 | 10/2002 | Wang et al. |
| 6,466,844 B1 | 10/2002 | Ikeda et al. |
| 6,468,265 B1 | 10/2002 | Evans et al. |
| 6,470,235 B2 | 10/2002 | Kasuga et al. |
| 6,474,434 B1 | 11/2002 | Bech |
| 6,480,762 B1 | 11/2002 | Uchikubo et al. |
| 6,491,701 B2 | 12/2002 | Tierney et al. |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury et al. |
| 6,523,629 B1 | 2/2003 | Buttz et al. |
| 6,526,332 B2 | 2/2003 | Sakamoto et al. |
| 6,529,620 B2 | 3/2003 | Thompson |
| 6,529,765 B1 | 3/2003 | Franck et al. |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu et al. |
| 6,543,899 B2 | 4/2003 | Covannon et al. |
| 6,549,215 B2 | 4/2003 | Jouppi |
| 6,563,533 B1 | 5/2003 | Colby |
| 6,567,038 B1 | 5/2003 | Granot et al. |
| 6,580,246 B2 | 6/2003 | Jacobs |
| 6,581,798 B2 | 6/2003 | Lift et al. |
| 6,584,376 B1 | 6/2003 | Van Kommer |
| 6,587,750 B2 | 7/2003 | Gerbi et al. |
| 6,590,604 B1 | 7/2003 | Tucker et al. |
| 6,594,269 B1 | 7/2003 | Polcyn |
| 6,594,552 B1 | 7/2003 | Nowlin et al. |
| 6,597,392 B1 | 7/2003 | Jenkins et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,604,022 B2 * | 8/2003 | Parker .................. G06N 3/008 700/250 |
| 6,611,120 B2 | 8/2003 | Song et al. |
| 6,643,496 B1 | 11/2003 | Shimoyama et al. |
| 6,646,677 B2 | 11/2003 | Noro et al. |
| 6,650,748 B1 | 11/2003 | Edwards et al. |
| 6,666,374 B1 | 12/2003 | Green et al. |
| 6,667,592 B2 | 12/2003 | Jacobs et al. |
| 6,674,259 B1 | 1/2004 | Norman et al. |
| 6,684,129 B2 | 1/2004 | Salisbury et al. |
| 6,691,000 B2 | 2/2004 | Nagai et al. |
| 6,693,585 B1 | 2/2004 | Macleod |
| 6,710,797 B1 | 3/2004 | Mcnelley et al. |
| 6,724,823 B2 | 4/2004 | Rovati et al. |
| 6,728,599 B2 | 4/2004 | Wang et al. |
| 6,763,282 B2 | 7/2004 | Glenn et al. |
| 6,764,373 B1 | 7/2004 | Osawa et al. |
| 6,769,771 B2 | 8/2004 | Trumbull |
| 6,781,606 B2 | 8/2004 | Jouppi |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,816,192 B1 | 11/2004 | Nishikawa |
| 6,816,754 B2 | 11/2004 | Mukai et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,856,662 B2 | 2/2005 | Glass et al. |
| 6,871,117 B2 | 3/2005 | Wang et al. |
| 6,879,879 B2 | 4/2005 | Jouppi et al. |
| 6,888,333 B2 | 5/2005 | Laby |

(56) References Cited

U.S. PATENT DOCUMENTS

| | | | |
|---|---|---|---|
| 6,892,112 B2 | 5/2005 | Wang et al. |
| 6,893,267 B1 | 5/2005 | Yueh |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe et al. |
| 6,957,712 B2 | 10/2005 | Song et al. |
| 6,958,706 B2 | 10/2005 | Chaco et al. |
| 6,965,394 B2 | 11/2005 | Gutta et al. |
| 6,990,112 B1 | 1/2006 | Brent et al. |
| 6,995,664 B1 | 2/2006 | Darling |
| 7,007,235 B1 | 2/2006 | Hussein et al. |
| 7,011,538 B2 | 3/2006 | Chang |
| 7,015,934 B2 | 3/2006 | Toyama et al. |
| 7,030,757 B2 | 4/2006 | Matsuhira et al. |
| RE39,080 E | 5/2006 | Johnston |
| 7,053,578 B2 | 5/2006 | Diehl et al. |
| 7,055,210 B2 | 6/2006 | Keppler et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | Mclurkin et al. |
| 7,123,285 B2 | 10/2006 | Smith et al. |
| 7,123,292 B1 | 10/2006 | Seeger et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Liff et al. |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 | 1/2007 | Wang et al. |
| 7,158,861 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,164,970 B2 | 1/2007 | Wang et al. |
| 7,167,448 B2 | 1/2007 | Wookey et al. |
| 7,171,286 B2 | 1/2007 | Wang et al. |
| 7,174,238 B1 | 2/2007 | Zweig |
| 7,181,455 B2 | 2/2007 | Wookey et al. |
| 7,184,559 B2 | 2/2007 | Jouppi |
| 7,188,000 B2 | 3/2007 | Chiappetta et al. |
| 7,199,790 B2 | 4/2007 | Rosenberg et al. |
| 7,202,851 B2 | 4/2007 | Cunningham et al. |
| 7,206,627 B2 | 4/2007 | Abovitz et al. |
| 7,215,786 B2 | 5/2007 | Nakadai et al. |
| 7,219,364 B2 | 5/2007 | Bolle et al. |
| 7,222,000 B2 | 5/2007 | Wang et al. |
| 7,227,334 B2 | 6/2007 | Yang et al. |
| 7,256,708 B2 | 8/2007 | Rosenfeld et al. |
| 7,262,573 B2 | 8/2007 | Wang et al. |
| 7,283,153 B2 | 10/2007 | Provost et al. |
| 7,289,883 B2 | 10/2007 | Wang et al. |
| 7,292,257 B2 | 11/2007 | Kang et al. |
| 7,292,912 B2 | 11/2007 | Wang et al. |
| 7,305,114 B2 | 12/2007 | Wolff et al. |
| 7,317,685 B1 | 1/2008 | Flott et al. |
| 7,321,807 B2 | 1/2008 | Laski |
| 7,332,890 B2 | 2/2008 | Cohen et al. |
| 7,333,642 B2 | 2/2008 | Green |
| 7,346,429 B2 | 3/2008 | Goldenberg et al. |
| 7,352,153 B2 | 4/2008 | Yan |
| 7,363,121 B1 | 4/2008 | Chen et al. |
| 7,382,399 B1 | 6/2008 | McCall et al. |
| 7,386,730 B2 | 6/2008 | Uchikubo |
| 7,391,432 B2 | 6/2008 | Terada |
| 7,400,578 B2 | 7/2008 | Guthrie et al. |
| 7,404,140 B2 | 7/2008 | O'Rourke |
| 7,421,470 B2 | 9/2008 | Ludwig et al. |
| 7,430,209 B2 | 9/2008 | Porter |
| 7,432,949 B2 | 10/2008 | Remy et al. |
| 7,433,921 B2 | 10/2008 | Ludwig et al. |
| 7,441,953 B2 | 10/2008 | Banks |
| 7,467,211 B1 | 12/2008 | Herman et al. |
| 7,483,867 B2 | 1/2009 | Ansari et al. |
| 7,492,731 B2 | 2/2009 | Hagendorf |
| 7,510,428 B2 | 3/2009 | Obata et al. |
| 7,523,069 B1 | 4/2009 | Friedl et al. |
| 7,525,281 B2 | 4/2009 | Koyanagi et al. |
| 7,535,486 B2 | 5/2009 | Motomura et al. |
| 7,557,758 B2 | 7/2009 | Rofougaran |
| 7,584,020 B2 * | 9/2009 | Bruemmer .............. G05D 1/024 701/25 |
| 7,587,260 B2 * | 9/2009 | Bruemmer .............. G06N 3/008 318/587 |
| 7,587,512 B2 | 9/2009 | Ta et al. |
| 7,590,060 B2 | 9/2009 | Miceli |
| 7,593,030 B2 | 9/2009 | Wang et al. |
| 7,599,290 B2 | 10/2009 | Dos Remedios et al. |
| 7,620,477 B2 * | 11/2009 | Bruemmer ........... G05D 1/0088 700/262 |
| 7,624,166 B2 | 11/2009 | Foote et al. |
| 7,630,314 B2 | 12/2009 | Dos Remedios et al. |
| 7,631,833 B1 | 12/2009 | Ghaleb et al. |
| 7,643,051 B2 | 1/2010 | Sandberg et al. |
| 7,647,320 B2 | 1/2010 | Mok et al. |
| 7,657,560 B1 | 2/2010 | Dirienzo |
| 7,668,621 B2 * | 2/2010 | Bruemmer .............. G06N 3/008 318/568.22 |
| 7,680,038 B1 | 3/2010 | Gourlay |
| 7,693,757 B2 | 4/2010 | Zimmerman |
| 7,698,432 B2 | 4/2010 | Short et al. |
| 7,703,113 B2 | 4/2010 | Dawson |
| 7,719,229 B2 | 5/2010 | Kaneko et al. |
| 7,737,993 B2 | 6/2010 | Kaasila et al. |
| 7,739,383 B1 | 6/2010 | Short et al. |
| 7,756,614 B2 | 7/2010 | Jouppi |
| 7,761,185 B2 | 7/2010 | Wang et al. |
| 7,769,492 B2 | 8/2010 | Wang et al. |
| 7,769,705 B1 | 8/2010 | Luechtefeld |
| 7,774,158 B2 | 8/2010 | Goncalves et al. |
| 7,801,644 B2 * | 9/2010 | Bruemmer .............. G06N 3/008 318/568.17 |
| 7,813,836 B2 | 10/2010 | Wang et al. |
| 7,831,575 B2 | 11/2010 | Trossell et al. |
| 7,835,775 B2 | 11/2010 | Sawayama et al. |
| 7,860,680 B2 | 12/2010 | Arms et al. |
| 7,861,366 B2 | 1/2011 | Hahm et al. |
| 7,873,448 B2 * | 1/2011 | Takeda ..................... G06T 7/73 701/28 |
| 7,885,822 B2 | 2/2011 | Akers et al. |
| 7,890,382 B2 | 2/2011 | Robb et al. |
| 7,912,583 B2 | 3/2011 | Gutmann et al. |
| RE42,288 E | 4/2011 | Degioanni |
| 7,924,323 B2 | 4/2011 | Walker et al. |
| 7,949,616 B2 | 5/2011 | Levy et al. |
| 7,956,894 B2 | 6/2011 | Akers et al. |
| 7,957,837 B2 | 6/2011 | Ziegler et al. |
| 7,974,738 B2 * | 7/2011 | Bruemmer ........... G05D 1/0088 318/568.18 |
| 7,982,763 B2 | 7/2011 | King |
| 7,982,769 B2 | 7/2011 | Jenkins et al. |
| 7,987,069 B2 | 7/2011 | Rodgers et al. |
| 8,073,564 B2 * | 12/2011 | Bruemmer .............. G06N 3/008 700/245 |
| 8,077,963 B2 * | 12/2011 | Wang ..................... A61B 34/70 382/153 |
| 8,116,910 B2 | 2/2012 | Walters et al. |
| 8,126,960 B2 | 2/2012 | Obradovich et al. |
| 8,170,241 B2 | 5/2012 | Roe et al. |
| 8,179,418 B2 | 5/2012 | Wright et al. |
| 8,180,486 B2 | 5/2012 | Saito et al. |
| 8,209,051 B2 | 6/2012 | Wang et al. |
| 8,212,533 B2 | 7/2012 | Ota |

(56) References Cited

U.S. PATENT DOCUMENTS

| | | | |
|---|---|---|---|
| 8,234,010 B2* | 7/2012 | Thompson | G05D 1/0227 901/46 |
| 8,265,793 B2 | 9/2012 | Cross et al. | |
| 8,271,132 B2* | 9/2012 | Nielsen | B25J 9/1666 700/250 |
| 8,287,522 B2 | 10/2012 | Moses et al. | |
| 8,292,807 B2 | 10/2012 | Perkins et al. | |
| 8,301,193 B1 | 10/2012 | Lynch et al. | |
| 8,320,534 B2 | 11/2012 | Kim et al. | |
| 8,340,654 B2 | 12/2012 | Bratton et al. | |
| 8,340,819 B2 | 12/2012 | Mangaser et al. | |
| 8,348,675 B2 | 1/2013 | Dohrmann | |
| 8,355,818 B2* | 1/2013 | Nielsen | G05D 1/0088 700/258 |
| 8,374,171 B2 | 2/2013 | Cho et al. | |
| 8,400,491 B1 | 3/2013 | Panpaliya et al. | |
| 8,401,229 B2 | 3/2013 | Hassan-Shafique et al. | |
| 8,401,275 B2 | 3/2013 | Wang et al. | |
| 8,423,284 B2 | 4/2013 | O'Shea | |
| 8,451,731 B1 | 5/2013 | Lee et al. | |
| 8,463,435 B2 | 6/2013 | Herzog et al. | |
| 8,489,234 B2* | 7/2013 | Rew | A47L 9/009 700/258 |
| 8,503,340 B1 | 8/2013 | Xu | |
| 8,515,577 B2 | 8/2013 | Wang et al. | |
| 8,527,094 B2 | 9/2013 | Kumar et al. | |
| 8,531,502 B2 | 9/2013 | Cheng et al. | |
| 8,532,860 B2 | 9/2013 | Daly | |
| 8,610,786 B2 | 12/2013 | Ortiz | |
| 8,612,051 B2 | 12/2013 | Normal et al. | |
| 8,620,077 B1 | 12/2013 | Grundmann et al. | |
| 8,632,376 B2* | 1/2014 | Dooley | A63F 13/803 901/6 |
| 8,639,797 B1 | 1/2014 | Pan et al. | |
| 8,670,017 B2 | 3/2014 | Stuart et al. | |
| 8,712,162 B2 | 4/2014 | Kirsch | |
| 8,718,837 B2* | 5/2014 | Wang | G05D 1/0274 382/209 |
| 8,726,454 B2 | 5/2014 | Gilbert et al. | |
| 8,836,751 B2 | 9/2014 | Ballantyne et al. | |
| 8,849,679 B2 | 9/2014 | Wang et al. | |
| 8,849,680 B2 | 9/2014 | Wright et al. | |
| 8,861,750 B2 | 10/2014 | Roe et al. | |
| 8,897,920 B2 | 11/2014 | Wang et al. | |
| 8,902,278 B2 | 12/2014 | Pinter et al. | |
| 8,935,005 B2* | 1/2015 | Rosenstein | G05D 1/0246 700/259 |
| 8,965,578 B2* | 2/2015 | Versteeg | G06N 3/004 700/258 |
| 8,965,579 B2 | 2/2015 | Wang et al. | |
| 8,983,772 B2 | 3/2015 | Lee | |
| 9,098,611 B2 | 8/2015 | Pinter et al. | |
| 9,147,284 B2 | 9/2015 | Keene | |
| 9,219,857 B2 | 12/2015 | Eldon | |
| 9,224,181 B2 | 12/2015 | Pinter et al. | |
| 9,323,250 B2* | 4/2016 | Wang | B25J 11/009 |
| 9,361,021 B2 | 6/2016 | Jordan et al. | |
| 9,469,030 B2 | 10/2016 | Wang | |
| 9,571,789 B2 | 2/2017 | Pinter et al. | |
| 9,776,327 B2* | 10/2017 | Pinter | G16H 40/67 |
| 9,785,149 B2 | 10/2017 | Wang et al. | |
| 9,902,069 B2* | 2/2018 | Farlow | B25J 11/009 |
| 10,328,576 B2* | 6/2019 | Pinter | G16H 40/67 |
| 10,780,582 B2* | 9/2020 | Pinter | G06Q 50/22 |
| 2001/0002448 A1 | 5/2001 | Wilson et al. | |
| 2001/0010053 A1 | 7/2001 | Ben-Shachar et al. | |
| 2001/0020200 A1 | 9/2001 | Das et al. | |
| 2001/0034475 A1 | 10/2001 | Flach et al. | |
| 2001/0034544 A1 | 10/2001 | Mo | |
| 2001/0037163 A1 | 11/2001 | Allard | |
| 2001/0048464 A1 | 12/2001 | Barnett | |
| 2001/0051881 A1 | 12/2001 | Filler | |
| 2001/0054071 A1 | 12/2001 | Loeb | |
| 2001/0055373 A1 | 12/2001 | Yamashita | |
| 2002/0013641 A1* | 1/2002 | Nourbakhsh | G05D 1/0214 700/245 |
| 2002/0015296 A1 | 2/2002 | Howell et al. | |
| 2002/0027597 A1 | 3/2002 | Sachau | |
| 2002/0027652 A1 | 3/2002 | Paromtchik et al. | |
| 2002/0030397 A1 | 3/2002 | Tamura et al. | |
| 2002/0033880 A1 | 3/2002 | Sul et al. | |
| 2002/0038168 A1 | 3/2002 | Kasuga et al. | |
| 2002/0044201 A1 | 4/2002 | Alexander et al. | |
| 2002/0049517 A1 | 4/2002 | Ruffner | |
| 2002/0055917 A1 | 5/2002 | Muraca | |
| 2002/0057279 A1 | 5/2002 | Jouppi | |
| 2002/0058929 A1 | 5/2002 | Green | |
| 2002/0059587 A1 | 5/2002 | Cofano et al. | |
| 2002/0063726 A1 | 5/2002 | Jouppi | |
| 2002/0073429 A1 | 6/2002 | Beane et al. | |
| 2002/0082498 A1 | 6/2002 | Wendt et al. | |
| 2002/0085030 A1 | 7/2002 | Ghani | |
| 2002/0086262 A1 | 7/2002 | Rainey | |
| 2002/0095238 A1 | 7/2002 | Ahlin et al. | |
| 2002/0095239 A1 | 7/2002 | Wallach et al. | |
| 2002/0098879 A1 | 7/2002 | Rheey | |
| 2002/0104094 A1 | 8/2002 | Alexander et al. | |
| 2002/0106998 A1 | 8/2002 | Presley et al. | |
| 2002/0109770 A1 | 8/2002 | Terada | |
| 2002/0109775 A1 | 8/2002 | White et al. | |
| 2002/0111988 A1 | 8/2002 | Sato | |
| 2002/0120362 A1 | 8/2002 | Lathan et al. | |
| 2002/0128985 A1 | 9/2002 | Greenwald | |
| 2002/0130950 A1 | 9/2002 | James et al. | |
| 2002/0133062 A1 | 9/2002 | Arling et al. | |
| 2002/0141595 A1 | 10/2002 | Jouppi | |
| 2002/0143923 A1 | 10/2002 | Alexander | |
| 2002/0177925 A1 | 11/2002 | Onishi et al. | |
| 2002/0183894 A1 | 12/2002 | Wang et al. | |
| 2002/0184674 A1 | 12/2002 | Xi et al. | |
| 2002/0186243 A1 | 12/2002 | Ellis et al. | |
| 2002/0198626 A1* | 12/2002 | Imai | G06N 3/008 700/245 |
| 2003/0016726 A1* | 1/2003 | Pavlidis | A61B 5/16 374/45 |
| 2003/0021107 A1 | 1/2003 | Howell et al. | |
| 2003/0030397 A1 | 2/2003 | Simmons | |
| 2003/0048481 A1 | 3/2003 | Kobayashi et al. | |
| 2003/0050733 A1 | 3/2003 | Wang et al. | |
| 2003/0050734 A1 | 3/2003 | Lapham | |
| 2003/0060808 A1 | 3/2003 | Wilk | |
| 2003/0063600 A1 | 4/2003 | Noma et al. | |
| 2003/0069752 A1 | 4/2003 | Ledain et al. | |
| 2003/0080901 A1 | 5/2003 | Piotrowski | |
| 2003/0100892 A1 | 5/2003 | Morley et al. | |
| 2003/0104806 A1 | 6/2003 | Ruef et al. | |
| 2003/0112823 A1 | 6/2003 | Collins et al. | |
| 2003/0114962 A1 | 6/2003 | Niemeyer | |
| 2003/0120714 A1 | 6/2003 | Wolff et al. | |
| 2003/0126361 A1 | 7/2003 | Slater et al. | |
| 2003/0135097 A1 | 7/2003 | Wiederhold et al. | |
| 2003/0135203 A1 | 7/2003 | Wang et al. | |
| 2003/0144579 A1 | 7/2003 | Buss | |
| 2003/0144649 A1 | 7/2003 | Ghodoussi et al. | |
| 2003/0151658 A1 | 8/2003 | Smith | |
| 2003/0152145 A1 | 8/2003 | Kawakita | |
| 2003/0171710 A1 | 9/2003 | Bassuk et al. | |
| 2003/0174285 A1 | 9/2003 | Trumbull | |
| 2003/0180697 A1 | 9/2003 | Kim et al. | |
| 2003/0195662 A1 | 10/2003 | Wang et al. | |
| 2003/0199000 A1 | 10/2003 | Valkirs et al. | |
| 2003/0206242 A1 | 11/2003 | Choi | |
| 2003/0212472 A1 | 11/2003 | McKee | |
| 2003/0216833 A1 | 11/2003 | Mukai et al. | |
| 2003/0216834 A1 | 11/2003 | Allard | |
| 2003/0220541 A1 | 11/2003 | Salisbury et al. | |
| 2003/0220715 A1 | 11/2003 | Kneifel et al. | |
| 2003/0231244 A1 | 12/2003 | Bonilla et al. | |
| 2003/0232649 A1 | 12/2003 | Gizis et al. | |
| 2003/0236590 A1 | 12/2003 | Park et al. | |
| 2004/0001197 A1 | 1/2004 | Ko et al. | |
| 2004/0001676 A1 | 1/2004 | Colgan et al. | |
| 2004/0008138 A1 | 1/2004 | George, Jr. et al. | |

(56) References Cited

U.S. PATENT DOCUMENTS

| | | |
|---|---|---|
| 2004/0009138 A1 | 1/2004 | Hockley, Jr. et al. |
| 2004/0010344 A1 | 1/2004 | Hiratsuka et al. |
| 2004/0012362 A1 | 1/2004 | Tsurumi |
| 2004/0013295 A1 | 1/2004 | Sabe et al. |
| 2004/0017475 A1 | 1/2004 | Akers et al. |
| 2004/0019406 A1 | 1/2004 | Wang et al. |
| 2004/0024490 A1 | 2/2004 | McLurkin et al. |
| 2004/0041904 A1 | 3/2004 | Lapalme et al. |
| 2004/0065073 A1 | 4/2004 | Nash |
| 2004/0068657 A1 | 4/2004 | Alexander et al. |
| 2004/0078219 A1 | 4/2004 | Kaylor et al. |
| 2004/0080610 A1 | 4/2004 | James et al. |
| 2004/0088077 A1 | 5/2004 | Jouppi et al. |
| 2004/0088078 A1 | 5/2004 | Jouppi et al. |
| 2004/0093409 A1 | 5/2004 | Thompson et al. |
| 2004/0095516 A1 | 5/2004 | Rohlicek |
| 2004/0098167 A1 | 5/2004 | Yi et al. |
| 2004/0102167 A1 | 5/2004 | Shim et al. |
| 2004/0107254 A1 | 6/2004 | Ludwig et al. |
| 2004/0107255 A1 | 6/2004 | Ludwig et al. |
| 2004/0117065 A1 | 6/2004 | Wang et al. |
| 2004/0117067 A1 | 6/2004 | Jouppi |
| 2004/0123158 A1 | 6/2004 | Roskind |
| 2004/0135879 A1 | 7/2004 | Stacy et al. |
| 2004/0138547 A1 | 7/2004 | Wang et al. |
| 2004/0140404 A1* | 7/2004 | Ohta .................... B64C 39/024 244/190 |
| 2004/0143421 A1 | 7/2004 | Wang et al. |
| 2004/0148638 A1 | 7/2004 | Weisman et al. |
| 2004/0150725 A1 | 8/2004 | Taguchi |
| 2004/0153211 A1 | 8/2004 | Kamoto et al. |
| 2004/0157612 A1 | 8/2004 | Kim |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0168148 A1 | 8/2004 | Goncalves et al. |
| 2004/0170300 A1 | 9/2004 | Jouppi |
| 2004/0172301 A1 | 9/2004 | Mihai et al. |
| 2004/0172306 A1 | 9/2004 | Wohl et al. |
| 2004/0174129 A1 | 9/2004 | Wang et al. |
| 2004/0175684 A1 | 9/2004 | Kaasa et al. |
| 2004/0179714 A1 | 9/2004 | Jouppi |
| 2004/0186623 A1 | 9/2004 | Dooley et al. |
| 2004/0189700 A1 | 9/2004 | Mandavilli et al. |
| 2004/0201602 A1 | 10/2004 | Mody et al. |
| 2004/0205664 A1 | 10/2004 | Prendergast |
| 2004/0215490 A1 | 10/2004 | Duchon et al. |
| 2004/0218099 A1 | 11/2004 | Washington |
| 2004/0222638 A1 | 11/2004 | Bednyak |
| 2004/0224676 A1 | 11/2004 | Iseki |
| 2004/0230340 A1 | 11/2004 | Fukuchi et al. |
| 2004/0236830 A1 | 11/2004 | Nelson |
| 2004/0240981 A1 | 12/2004 | Dothan et al. |
| 2004/0241981 A1 | 12/2004 | Doris et al. |
| 2004/0260790 A1 | 12/2004 | Balloni et al. |
| 2005/0003330 A1 | 1/2005 | Asgarinejad et al. |
| 2005/0004708 A1 | 1/2005 | Goldenberg et al. |
| 2005/0007445 A1 | 1/2005 | Foote et al. |
| 2005/0013149 A1 | 1/2005 | Trossell |
| 2005/0021182 A1 | 1/2005 | Wang et al. |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka et al. |
| 2005/0065813 A1 | 3/2005 | Mishelevich et al. |
| 2005/0071046 A1 | 3/2005 | Miyazaki et al. |
| 2005/0073575 A1 | 4/2005 | Thacher et al. |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovynin |
| 2005/0110867 A1 | 5/2005 | Schulz |
| 2005/0122390 A1 | 6/2005 | Wang et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | McGee et al. |
| 2005/0264649 A1 | 12/2005 | Chang et al. |
| 2005/0267826 A1 | 12/2005 | Levy et al. |
| 2005/0278446 A1 | 12/2005 | Bryant |
| 2005/0283414 A1 | 12/2005 | Fernandes et al. |
| 2005/0286759 A1 | 12/2005 | Zitnick et al. |
| 2006/0007943 A1 | 1/2006 | Fellman |
| 2006/0010028 A1 | 1/2006 | Sorensen |
| 2006/0013263 A1 | 1/2006 | Fellman |
| 2006/0013469 A1 | 1/2006 | Wang et al. |
| 2006/0013488 A1 | 1/2006 | Inoue |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |
| 2006/0048286 A1 | 3/2006 | Donato |
| 2006/0052676 A1 | 3/2006 | Wang et al. |
| 2006/0052684 A1 | 3/2006 | Takahashi et al. |
| 2006/0056655 A1 | 3/2006 | Wen et al. |
| 2006/0056837 A1 | 3/2006 | Vapaakoski |
| 2006/0064212 A1 | 3/2006 | Thorne |
| 2006/0066609 A1 | 3/2006 | Iodice et al. |
| 2006/0071797 A1 | 4/2006 | Rosenfeld et al. |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0122482 A1 | 6/2006 | Mariotti et al. |
| 2006/0125356 A1 | 6/2006 | Meek et al. |
| 2006/0142983 A1 | 6/2006 | Sorensen et al. |
| 2006/0149418 A1 | 7/2006 | Anvari |
| 2006/0161136 A1 | 7/2006 | Anderson et al. |
| 2006/0161303 A1 | 7/2006 | Wang et al. |
| 2006/0164546 A1 | 7/2006 | Adachi |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178559 A1 | 8/2006 | Kumar et al. |
| 2006/0178776 A1 | 8/2006 | Feingold et al. |
| 2006/0178777 A1 | 8/2006 | Park et al. |
| 2006/0184274 A1 | 8/2006 | Sakai et al. |
| 2006/0189393 A1 | 8/2006 | Edery |
| 2006/0195569 A1 | 8/2006 | Barker |
| 2006/0224781 A1 | 10/2006 | Tsao et al. |
| 2006/0247045 A1 | 11/2006 | Jeong et al. |
| 2006/0259193 A1 | 11/2006 | Wang et al. |
| 2006/0268704 A1 | 11/2006 | Ansari et al. |

(56) References Cited

U.S. PATENT DOCUMENTS

| | | |
|---|---|---|
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0008321 A1 | 1/2007 | Gallagher et al. |
| 2007/0016328 A1* | 1/2007 | Ziegler .................. A47L 9/009 701/23 |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0061041 A1 | 3/2007 | Zweig |
| 2007/0064092 A1 | 3/2007 | Sandberg et al. |
| 2007/0070069 A1 | 3/2007 | Samarasekera |
| 2007/0078566 A1 | 4/2007 | Wang et al. |
| 2007/0093279 A1 | 4/2007 | Janik |
| 2007/0109324 A1 | 5/2007 | Lin |
| 2007/0112700 A1 | 5/2007 | Den et al. |
| 2007/0116152 A1 | 5/2007 | Thesling |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0156286 A1* | 7/2007 | Yamauchi ............ G05D 1/0278 700/245 |
| 2007/0170886 A1 | 7/2007 | Plishner |
| 2007/0176060 A1 | 8/2007 | White et al. |
| 2007/0182811 A1 | 8/2007 | Rockefeller et al. |
| 2007/0192910 A1* | 8/2007 | Vu ........................ B25J 19/06 901/17 |
| 2007/0197896 A1 | 8/2007 | Moll et al. |
| 2007/0198128 A1* | 8/2007 | Ziegler .................. G06N 3/008 700/245 |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0226949 A1 | 10/2007 | Hahm et al. |
| 2007/0234492 A1* | 10/2007 | Svendsen ................ B60L 50/52 15/97.1 |
| 2007/0250212 A1 | 10/2007 | Halloran et al. |
| 2007/0255115 A1* | 11/2007 | Anglin, Jr. ............ G16H 10/60 600/300 |
| 2007/0255155 A1 | 11/2007 | Drew et al. |
| 2007/0255706 A1 | 11/2007 | Iketani et al. |
| 2007/0262884 A1 | 11/2007 | Goncalves et al. |
| 2007/0273751 A1 | 11/2007 | Sachau |
| 2007/0290040 A1 | 12/2007 | Wurman et al. |
| 2007/0291109 A1 | 12/2007 | Wang et al. |
| 2007/0291128 A1 | 12/2007 | Wang et al. |
| 2008/0009969 A1 | 1/2008 | Bruemmer et al. |
| 2008/0011904 A1 | 1/2008 | Cepollina et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D'Andrea et al. |
| 2008/0056933 A1 | 3/2008 | Moore et al. |
| 2008/0065268 A1 | 3/2008 | Wang et al. |
| 2008/0082211 A1 | 4/2008 | Wang et al. |
| 2008/0086236 A1* | 4/2008 | Saito .................. G05D 1/0251 901/1 |
| 2008/0086241 A1 | 4/2008 | Phillips et al. |
| 2008/0091340 A1 | 4/2008 | Milstein et al. |
| 2008/0126132 A1 | 5/2008 | Warner et al. |
| 2008/0133052 A1 | 6/2008 | Jones et al. |
| 2008/0161969 A1 | 7/2008 | Lee et al. |
| 2008/0174570 A1 | 7/2008 | Jobs et al. |
| 2008/0201016 A1 | 8/2008 | Finlay |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0232763 A1 | 9/2008 | Brady |
| 2008/0242220 A1 | 10/2008 | Wilson |
| 2008/0255703 A1 | 10/2008 | Wang et al. |
| 2008/0263451 A1 | 10/2008 | Portele et al. |
| 2008/0263628 A1 | 10/2008 | Normal et al. |
| 2008/0267069 A1 | 10/2008 | Thielman et al. |
| 2008/0269949 A1 | 10/2008 | Normal et al. |
| 2008/0281467 A1 | 11/2008 | Pinter |
| 2008/0285886 A1 | 11/2008 | Allen |
| 2008/0306375 A1 | 12/2008 | Sayler et al. |
| 2008/0316368 A1* | 12/2008 | Fritsch .................. H04N 5/272 348/E5.022 |
| 2009/0021572 A1 | 1/2009 | Garudadri et al. |
| 2009/0030552 A1* | 1/2009 | Nakadai .............. G10L 21/028 704/275 |
| 2009/0044334 A1 | 2/2009 | Parsell et al. |
| 2009/0049640 A1 | 2/2009 | Lee et al. |
| 2009/0055019 A1* | 2/2009 | Stiehl .................. B25J 9/1671 901/17 |
| 2009/0055023 A1 | 2/2009 | Walters et al. |
| 2009/0070135 A1 | 3/2009 | Parida et al. |
| 2009/0086013 A1 | 4/2009 | Thapa |
| 2009/0102919 A1 | 4/2009 | Zamierowski et al. |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0125584 A1 | 5/2009 | Agrawala et al. |
| 2009/0144425 A1 | 6/2009 | Marr et al. |
| 2009/0146882 A1 | 6/2009 | Halivaara et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0177323 A1 | 7/2009 | Ziegler et al. |
| 2009/0177641 A1 | 7/2009 | Raghavan |
| 2009/0201372 A1 | 8/2009 | O'Doherty et al. |
| 2009/0210090 A1* | 8/2009 | Takemitsu ............ B25J 9/1661 901/1 |
| 2009/0237317 A1 | 8/2009 | Rofougaran |
| 2009/0234499 A1 | 9/2009 | Nielsen et al. |
| 2009/0240371 A1 | 9/2009 | Wang et al. |
| 2009/0248200 A1 | 10/2009 | Root |
| 2009/0259339 A1 | 10/2009 | Wright et al. |
| 2009/0323648 A1 | 12/2009 | Park et al. |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |
| 2010/0030378 A1* | 2/2010 | Choi .......................... G01S 1/54 901/1 |
| 2010/0030578 A1 | 2/2010 | Siddique et al. |
| 2010/0037418 A1* | 2/2010 | Hussey ................ G05D 1/0234 901/1 |
| 2010/0041998 A1 | 2/2010 | Postel et al. |
| 2010/0051596 A1 | 3/2010 | Diedrick et al. |
| 2010/0063636 A1* | 3/2010 | Matsumoto ............ F24F 11/63 700/276 |
| 2010/0063848 A1 | 3/2010 | Kremer et al. |
| 2010/0066804 A1 | 3/2010 | Shoemake et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0128104 A1 | 5/2010 | Fabregat et al. |
| 2010/0131103 A1 | 5/2010 | Herzog et al. |
| 2010/0145479 A1 | 6/2010 | Griffiths |
| 2010/0153317 A1* | 6/2010 | Lee ........................ B25J 9/1661 901/50 |
| 2010/0157825 A1 | 6/2010 | Anderlind et al. |
| 2010/0171826 A1 | 7/2010 | Hamilton et al. |
| 2010/0191375 A1 | 7/2010 | Wright et al. |
| 2010/0228249 A1 | 9/2010 | Mohr et al. |
| 2010/0243344 A1* | 9/2010 | Wyrobek ............ B25J 19/0016 180/21 |
| 2010/0253775 A1 | 10/2010 | Yamaguchi |
| 2010/0268383 A1 | 10/2010 | Wang et al. |
| 2010/0278086 A1 | 11/2010 | Pochiraju et al. |

(56) References Cited

U.S. PATENT DOCUMENTS

| | | |
|---|---|---|
| 2010/0286905 A1 | 11/2010 | Goncalves et al. |
| 2010/0301679 A1 | 12/2010 | Murray et al. |
| 2010/0315352 A1 | 12/2010 | Hamamura |
| 2010/0323783 A1 | 12/2010 | Nonaka et al. |
| 2011/0022705 A1 | 1/2011 | Yellamraju et al. |
| 2011/0050841 A1 | 3/2011 | Wang et al. |
| 2011/0071672 A1* | 3/2011 | Sanders ............... B25J 9/161 700/245 |
| 2011/0071675 A1 | 3/2011 | Wells et al. |
| 2011/0071702 A1 | 3/2011 | Wang et al. |
| 2011/0072114 A1 | 3/2011 | Hoffert et al. |
| 2011/0077852 A1 | 3/2011 | Ragavan et al. |
| 2011/0153198 A1 | 6/2011 | Kokkas et al. |
| 2011/0169832 A1 | 7/2011 | Brown et al. |
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0193949 A1 | 8/2011 | Nambakam et al. |
| 2011/0195701 A1 | 8/2011 | Temby et al. |
| 2011/0213210 A1 | 9/2011 | Temby et al. |
| 2011/0218674 A1 | 9/2011 | Stuart et al. |
| 2011/0231050 A1* | 9/2011 | Goulding ............. G05D 1/0891 180/8.1 |
| 2011/0231796 A1 | 9/2011 | Vigil |
| 2011/0245973 A1 | 10/2011 | Wang et al. |
| 2011/0249079 A1 | 10/2011 | Santamaria et al. |
| 2011/0280551 A1 | 11/2011 | Sammon |
| 2011/0288417 A1 | 11/2011 | Pinter et al. |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0023506 A1 | 1/2012 | Maeckel et al. |
| 2012/0036484 A1 | 2/2012 | Zhang et al. |
| 2012/0059946 A1 | 3/2012 | Wang |
| 2012/0072023 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0113856 A1 | 5/2012 | Krishnaswamy |
| 2012/0182392 A1* | 7/2012 | Kearns ............... B25J 19/023 348/46 |
| 2012/0185095 A1* | 7/2012 | Rosenstein ......... G05D 1/0227 901/1 |
| 2012/0191246 A1 | 7/2012 | Roe et al. |
| 2012/0191464 A1 | 7/2012 | Stuart et al. |
| 2012/0203731 A1 | 8/2012 | Nelson et al. |
| 2012/0215380 A1 | 8/2012 | Fouillade et al. |
| 2012/0215830 A1 | 8/2012 | Anguiano |
| 2012/0218374 A1 | 8/2012 | Matula et al. |
| 2012/0220372 A1 | 8/2012 | Cheung et al. |
| 2012/0291809 A1 | 11/2012 | Kuhe et al. |
| 2012/0176525 A1 | 12/2012 | Garin |
| 2012/0316676 A1 | 12/2012 | Fouillade et al. |
| 2013/0002794 A1 | 1/2013 | Hines et al. |
| 2013/0035790 A1* | 2/2013 | Olivier, III .......... G05D 1/0246 901/1 |
| 2013/0065604 A1 | 3/2013 | Werner et al. |
| 2013/0113871 A1 | 5/2013 | Ballantyne et al. |
| 2013/0158720 A1 | 6/2013 | Zywicki et al. |
| 2013/0166137 A1* | 6/2013 | Ahn .................. G05D 1/027 701/32.3 |
| 2013/0250938 A1 | 9/2013 | Anandakumar et al. |
| 2013/0275922 A1 | 10/2013 | Pinter et al. |
| 2013/0325244 A1 | 12/2013 | Wang et al. |
| 2014/0015914 A1 | 1/2014 | Dalaunay |
| 2014/0047022 A1 | 2/2014 | Chan et al. |
| 2014/0085543 A1 | 3/2014 | Hartley et al. |
| 2014/0128103 A1 | 5/2014 | Joao et al. |
| 2014/0135990 A1 | 5/2014 | Stuart et al. |
| 2014/0139616 A1 | 5/2014 | Pinter et al. |
| 2014/0155755 A1 | 6/2014 | Pinter et al. |
| 2014/0207286 A1 | 7/2014 | Wang et al. |
| 2014/0254896 A1* | 9/2014 | Zhou ................ G05D 1/0278 705/16 |
| 2014/0267549 A1 | 9/2014 | Pinter et al. |
| 2014/0302931 A1* | 10/2014 | Conceicao ............. A63F 13/20 463/31 |
| 2015/0077502 A1 | 3/2015 | Jordan et al. |
| 2015/0081338 A1 | 3/2015 | Lai et al. |
| 2015/0088310 A1 | 3/2015 | Pinter et al. |
| 2015/0296177 A1 | 10/2015 | Pinter et al. |
| 2015/0314449 A1 | 11/2015 | Wang et al. |
| 2016/0167231 A1* | 6/2016 | Nakayama ............. B25J 9/1694 700/255 |
| 2016/0229058 A1 | 8/2016 | Pinter et al. |
| 2016/0283685 A1 | 8/2016 | Pinter et al. |
| 2016/0358276 A1* | 12/2016 | Stephenson ............ G16H 20/00 |
| 2017/0023944 A1 | 1/2017 | Wang et al. |
| 2017/0106738 A1* | 4/2017 | Gillett .................... B62K 25/02 |
| 2017/0127019 A1 | 5/2017 | Pinter et al. |
| 2017/0144299 A1* | 5/2017 | Lafaye ..................... B25J 9/162 |
| 2018/0099412 A1 | 4/2018 | Pinter et al. |
| 2020/0009736 A1 | 1/2020 | Pinter et al. |

FOREIGN PATENT DOCUMENTS

| | | |
|---|---|---|
| CN | 1404695 | 3/2003 |
| CN | 1554193 | 12/2004 |
| CN | 1554985 | 12/2004 |
| CN | 1561923 | 1/2005 |
| CN | 1743144 | 3/2006 |
| CN | 101049017 | 10/2007 |
| CN | 101106939 | 1/2008 |
| CN | 101151614 | 3/2008 |
| CN | 100407729 | 7/2008 |
| CN | 101390098 | 3/2009 |
| CN | 101507260 | 8/2009 |
| CN | 101730894 | 6/2010 |
| CN | 101866396 | 10/2010 |
| CN | 101978365 | 2/2011 |
| CN | 102203759 | 9/2011 |
| EP | 466492 | 1/1992 |
| EP | 488673 | 6/1992 |
| EP | 981905 | 1/2002 |
| EP | 1262142 | 12/2002 |
| EP | 1304872 | 4/2003 |
| EP | 1536660 | 6/2005 |
| EP | 1573406 | 9/2005 |
| EP | 1594660 | 11/2005 |
| EP | 1763243 | 3/2007 |
| EP | 1791464 | 6/2007 |
| EP | 1800476 | 6/2007 |
| EP | 1819108 | 8/2007 |
| EP | 1856644 | 11/2007 |
| EP | 1928310 | 6/2008 |
| EP | 1232610 | 1/2009 |
| EP | 2027716 | 2/2009 |
| EP | 2145274 | 1/2010 |
| EP | 2214111 | 8/2010 |
| EP | 2263158 | 12/2010 |
| EP | 2300930 | 3/2011 |
| EP | 2342651 | 7/2011 |
| GB | 2431261 | 4/2007 |
| JP | 7-194609 | 8/1995 |
| JP | 7-213753 | 8/1995 |
| JP | 7-248823 | 9/1995 |
| JP | 7-257422 | 10/1995 |
| JP | 8-084328 | 3/1996 |
| JP | 8-166822 | 6/1996 |
| JP | 8-320727 | 12/1996 |
| JP | 9-267276 | 10/1997 |
| JP | 10-79097 | 3/1998 |
| JP | 10-288689 | 10/1998 |
| JP | 11-220706 | 8/1999 |
| JP | 2000-032319 | 1/2000 |
| JP | 2000-049800 | 2/2000 |
| JP | 2000-079587 | 3/2000 |
| JP | 2000-196876 | 7/2000 |
| JP | 2001-125641 | 5/2001 |
| JP | 2001-147718 | 5/2001 |
| JP | 2001-179663 | 7/2001 |
| JP | 2001-188124 | 7/2001 |
| JP | 2001-198865 | 7/2001 |

(56) References Cited

FOREIGN PATENT DOCUMENTS

| | | |
|---|---|---|
| JP | 2001-198868 | 7/2001 |
| JP | 2001-199356 | 7/2001 |
| JP | 2002-000574 | 1/2002 |
| JP | 2002-046088 | 2/2002 |
| JP | 2002-101333 | 4/2002 |
| JP | 2002-112970 | 4/2002 |
| JP | 2002-235423 | 8/2002 |
| JP | 2002-305743 | 10/2002 |
| JP | 2002-321180 | 11/2002 |
| JP | 2002-355779 | 12/2002 |
| JP | 2004-181229 | 7/2004 |
| JP | 2004-424824 | 8/2004 |
| JP | 2004-261941 | 9/2004 |
| JP | 2004-289379 | 10/2004 |
| JP | 2005-028066 | 2/2005 |
| JP | 2005-059170 | 3/2005 |
| JP | 2005-111083 | 4/2005 |
| JP | 2006-35381 | 2/2006 |
| JP | 2006-508806 | 3/2006 |
| JP | 2006-109094 | 4/2006 |
| JP | 2006-224294 | 8/2006 |
| JP | 2006-246438 | 9/2006 |
| JP | 2007-007040 | 1/2007 |
| JP | 2007-081646 | 3/2007 |
| JP | 2007-232208 | 9/2007 |
| JP | 2007-316966 | 12/2007 |
| JP | 2009-125133 | 9/2009 |
| JP | 2010-064154 | 3/2010 |
| JP | 2010-532109 | 9/2010 |
| JP | 2010-246954 | 11/2010 |
| KR | 2006-0037979 | 5/2006 |
| KR | 2009-0012542 | 2/2009 |
| KR | 2010-0019479 | 2/2010 |
| KR | 2010-0139037 | 12/2010 |
| WO | 93/06690 | 4/1993 |
| WO | 97/42761 | 11/1997 |
| WO | 1998/51078 | 11/1998 |
| WO | 99/67067 | 12/1999 |
| WO | 2000/025516 | 5/2000 |
| WO | 2000/033726 | 6/2000 |
| WO | 2001/31861 | 5/2001 |
| WO | 2003/077745 | 9/2003 |
| WO | 2004/008738 | 1/2004 |
| WO | 2004/012018 | 2/2004 |
| WO | 2004/075456 | 9/2004 |
| WO | 2006/012797 | 2/2006 |
| WO | 2006/044847 | 4/2006 |
| WO | 2006/078611 | 7/2006 |
| WO | 2007041295 | 4/2007 |
| WO | 2007/041038 | 6/2007 |
| WO | 2008/100272 | 10/2008 |
| WO | 2009/117274 | 9/2009 |
| WO | 2009/128997 | 10/2009 |
| WO | 2009/145958 | 12/2009 |
| WO | 2010/006205 | 1/2010 |
| WO | 2010/006211 | 1/2010 |
| WO | 2010/033666 | 3/2010 |
| WO | 2010/047881 | 4/2010 |
| WO | 2010/062798 | 6/2010 |
| WO | 2010/065257 | 6/2010 |
| WO | 2010/120407 | 10/2010 |
| WO | 2011/028589 | 3/2011 |
| WO | 2011/097130 | 8/2011 |
| WO | 2011/097132 | 8/2011 |
| WO | 2011/109336 | 9/2011 |
| WO | 2011/149902 | 12/2011 |
| WO | 2013/097264 | 7/2013 |
| WO | 2013/176762 A1 | 11/2013 |

OTHER PUBLICATIONS

"Magne Charge," Smart Power of Electric Vehicles, Aug. 26, 1997, 2 pages.

"More Online Robots: Robots that Manipulate," available on-line at http://ford.ieor.berkeley.edu/ir/robots_a2.html, Retrieived on Nov. 23, 2010, Aug. 2001, 2 pages.

"MPEG File Format Summary," available online at http://www.fileformat.info/format/mpeg/egff.htm, Feb. 1, 2001, 8 pages.

"Nomad Scout Language Reference Manual," Nomadic Technologies, Software Version 2.7, Part No. DOC00002, Jul. 12, 1999, 47 pages.

"Robart I, II, III," Spawar, Systems Center Pacific, 1998, 8 pages.

ACM Digital Library Record, Autonomous Robots vol. II Issue 1, available online at http://dl.acm.org/citation.cfm?id=591550&picked=prox&cfid=360891374&cftoken=35225929, Jul. 2001, 2 pages.

Active Media, Inc., "Saphira Software Manual," Saphira Version 5.3, 1997, 105 pages.

Activmedia Robotics, "Pioneer2/PeopleBot TM," Operations Manual, Version 9, Oct. 2001, 78 pages.

Adams, Chris, "Simulation of Adaptive Behavior (SAB'02)," Mobile Robotics Research Group, The Seventh International Conference, retrieved on Jan. 22, 2014, available online at http://www.dai.ed.ac.uk/groups/mrg/MG.html, Aug. 4-11, 2002, 1 page.

Al-Kassab et al., "A Review of Telemedicine," Journal of Telemedicine and Telecare, vol. 5, Supplement 1, 1999, pp. 103-106.

Ando et al., "A Multimedia Self-service Terminal with Conferencing Functions," Robot and Human Communication, Tokyo, Proceedings of $4^{th}$ IEEE International Workshop, Jul. 5-7, 1995, pp. 357-362.

Android Amusement Corp., "What Marketing Secret Renting Robots from Android Amusement Corp!", (Advertisement), 1982, 1 page.

Appeal from the U.S. District Court for the Central District of California in case No. 11-cv-9185, Judge Percy Anderson, Joint Appendix, vol. 1 of IV, Jun. 24, 2013, pp. A1-A6357.

Appeal from the U.S. District Court for the Central District of California in case No. 11-cv-9185, Judge Percy Anderson, Joint Appendix, vol. II of IV, Jun. 24, 2013, pp. A6849-A10634.

Appeal from the U.S. District Court for the Central District of California in case No. 11-cv-9185, Judge Percy Anderson, Joint Appendix, vol. III of IV, Jun. 24, 2013, pp. A10654-A15517.

Appeal from the U.S. District Court for the Central District of California in case No. 11-cv-9185, Judge Percy Anderson, Joint Appendix, vol. IV of IV, Jun. 24, 2013, pp. A15677-A18127.

Appeal from the U.S. District Court for the Central District of California in case No. 11-cv-9185, Judge Percy Anderson, May 9, 2014, pp. 1-48.

Apple Inc., "I Phone," iPhone Series, XP002696350, Sep. 21, 2012, pp. 1-29.

Applebome, Peter, "Planning Domesticated Robots for Tomorrow's Household," New York Times, available on-line at http://www.theoldrobots.com/images17/dc17.jpg, Mar. 4, 1982, pp. 21 and 23.

Bar-Cohen et al., "Virtual Reality Robotic Telesurgery Simulations Using MEMICA Haptic System," Proceedings of SPIE's $8^{th}$ Annual International Symposium on Smart Structures and Materials, Mar. 5-8, 2001, pp. 1-7.

Barrett, Rick, "Video Conferencing Business Soars as Companies Cut Travel; Some Travel Cuts are Permanent," available online at http://www.ivci.com/international_videoconferencing_news_videoconferencing_news_19.html, May 13, 2002, 2 pages.

Bartholomew, "Pharmacy Apothecary," available online at http://classes.bnf.fr/ema/grands/034.htm, retrieved on Jul. 26, 2012, 2 pages.

Bauer et al., "Remote Telesurgical Mentoring: Feasibility and Efficacy," IEEE, Proceedings of the $33^{rd}$ Hawaii International Conference on System Sciences, 2000, pp. 1-9.

Bauer, Jeffrey C., "Service Robots in Health Care: The Evolution of Mechanical Solutions to Human Resource Problems," Bon Secours Health System Inc., Technology Early Warning System (TEWS), Future of Service Robots in Health Care, Jun. 2003, pp. 1-10.

Bischoff, Rainer, "Design Concept and Realization of the Humanoid Service Robot HERMES," Field and Service Robotics, Springer, 1998, pp. 485-492.

Blackwell, Gerry, "Video: A Wireless LAN Killer App?" available online at http://www.wi-fiplanet.com/columns/article.php/1010261/Video-A-Wireless-LAN-Killer, Apr. 16, 2002 4 pages.

(56) References Cited

OTHER PUBLICATIONS

Blaer et al., "TopBot: Automated Network Topology Detection with a Mobile Robot", IEEE, Proceedings of the 2003 International Conference on Robotics 7 Automation, Taipei, Taiwan, Sep. 14-19, 2003, pp. 1582-1587.
Bradner, S., "The Internet Standards Process—Revision 3", Network Working Group, Request for Comments: 2026, BCP 9, Obsoletes: 1602, Category: Best Current Practice, Oct. 1996, pp. 1-36.
Brenner, Pablo, "A Technical Tutorial on the IEEE 802.11 Protocol," Breezecom Wireless Communications, 1997, pp. 1-24.
Breslow et al., "Effect of a Multiple-Site Intensive Care Unit Telemedicine Program on Clinical and Economic Outcome an Alternative Paradigm for Intensivist Staffing," Critical Care Med, vol. 32, No. 1, Jan. 2004, pp. 31-38.
Brooks, Rodney Allen, "Remote Presence," Abstracts from Flesh & Machines, How Robots Will Change Us, Feb. 2002, pp. 131-147.
Brooks, Rodney, "A Robust Layered Control System for a Mobile Robot," IEEE, Journal of Robotics and Automation, vol. 2, No. 1, Mar. 1986, pp. 14-23.
Cell et al., "The eICU: It's Not Just Telemedicine," Critical Care Medicine, vol. 29, No. 8 (Supplement), Aug. 2001, pp. 183-189.
Cheetham et al., "Interface Development for a Child's Video Conferencing Robot," available online at www.ryerson.ca/pebbles/publications/paper-iea200hfes-last.pdf, 2000, 4 pages.
Christensen et al., "BeeSoft User's Guide and Reference," Robots for the Real Word™, Real World Interface, Inc., Sep. 26, 1997, 203 pages.
Chu et al., "Detection of Target Mobile Signal Strength," Technical Development, Motorola Inc., Jan. 1999, pp. 205-206.
Civil Minutes—General: Case No. CV 11-9185PA (AJWx), *InTouch Tech.*, v. *VGO Commons, Inc.*, Sep. 10, 2012, 7 pages.
Cleary et al., "State of the Art in Surgical Robotics: Clinical Applications and Technology Challenges," Feb. 24, 2002, pp. 1-26.
CMU Course 16X62, "Robot User's Manual," (describing the Nomad Scout), Carnegie Mellon University, Feb. 1, 2001, 11 pages.
CNN, "Floating 'Droids' to Roam Apace Corridors of the Future," Available online at http://edition.cnn.com/2000/TECH/space/01/12/psa/, Jan. 12, 2000, 3 pages.
CNN.com, "Paging Dr. Robot: Machine Helps Doctors with Patients," Sep. 30, 2003, 3 pages.
Crowley, Susan L., "Hello to Our Future," AARP Bulletin, Jan. 2000, 12 pages.
Dalton, Barnaby, "Techniques for Web Telerobotics," PhD Thesis, University of Western Australia, 2001, 243 pages.
Dario et al., "A Robot Workstation for Diagnosis and Physical Therapy," IEEE Catalog No. 88$^{TH}$0234-5, 1989, pp. 67-72.
Davies, Brian, "Robotics in Minimall Invasive Surgery," IEE Colloquium on Through the Keyhole: Microengineering in Minimally Invasive Surgery, 1995, pp. 1-2.
Davis, Erik, "Telefriend, Meet iRobot, The Smartest Webcam on Wheels," Wired Magazine, Issue 8.09, Available online at http://www.wired.com/wired/archive/8.09/irobot.html?pg=1&topic=&topic_set+, Sep. 200, 3 pages.
Dean et al., "1992 AAAI Robot Exhibition and Competition," Articles, AI Magazine, vol. 14, No. 1, 1993, 15 pages.
Defendant VGO Communications, Inc.'s Invalidity Contentions Pursuant to the Feb. 27, 2012 Civil Minutes Order, May 2, 2012, 143 pages.
Defendant-Counterclaimant VGO Communications, Inc.'s Supplemental Invalidity Contentions Pursuant to the Feb. 27, 2012 Civil Minute Order, May 14, 2012, 228 pages.
Digiorgio, James, "Is Your Emergency Department of the Leading Edge," Chicago Hospital News, vol. 2, No. 12, 2005, 3 pages.
Dudenhoeffer et al., "Command and Control Architectures for Autonomous Micro-Robotic Forces," FY00 Project Report, Idaho National Engineering and Environmental Laboratory Human Systems Engineering and Sciences Department, Idaho Falls, Apr. 2001, 32 pages.
Elhajj et al., "Real-Time Haptic Feedback in Internet-Based Telerobotic Operation," IEEE International Conference on Electro/information Technology, available online at http://www.egr.msu.edu~ralab-web/cgi_bin/internet-teleoperation.php, Jun. 2000, 10 pages.
Elhajj et al., "Supermedia in Internet-Based Telerobotic Operaitons," Management of Multimedia on the Internet Lecture Notes in Computer Science, Springer-Verlag Berlin Heidelberg, vol. 2216, Oct. 29-Nov. 1, 2001, pp. 359-372.
Elhajj et al., "Synchronization and Control of Supermedia Transmission Via the Internet," Proceedings of 2001 International Symposium on Intelligent Multimedia and Speech Processing, May 2-4, 2001, pp. 320-323.
Ellison et al., "Telerounding and Patient Satisfaction Following Surgery," vol. 199, No. 4, Oct. 2004, pp. 523-530.
Evans et al., "The Trackless Robotic Courier," PYXIS HelpMate®, 2007, 3 pages.
Fels et al., "Developing a Video-Mediated Communication System for Hospitalized Children," Telemedicine Journal, vol. 5, No. 2, 1999, 30 pages.
Fetterman et al., "Videoconferencing Over the Internet," 2001, 8 pages.
Florini et al., "Health Care Robotics: A Progress Report," IEEE International Conference on Robotics and Automation, Apr. 20-25, 1997, pp. 1271-1276.
Fong, Terreance, "Collaborative Control: A Robot-Centric Model for Vehicle Teleoperation," Doctoral Dissertation Technical Report CMU-RI-TR-01-34, Robotics Institute, Carnegie Mellon University, Nov. 2001,197 pages.
Fulbright et al., "SWAMI: An Autonomous Mobile Robot for Inspection of Nuclear Waste of Storage Facilities," Autonomous Robots, vol. 2, 1995, pp. 225-235.
Gaidioz et al. "Synchronizing Network Probes to Avoid Measurement Intrusiveness with the Network Weather Service," Proceedings of the Ninth International Symposium on High-Performance Distributed Computing, 2000, pp. 137-154.
Garner et al., "The Application of Telepresence in Medicine," BT Technology Journal, vol. 15, No. 4, Oct. 1, 1997, pp. 181-187.
Ghiasi et al., "A Generic Web-based Teleoperations Architecture: Details and Experience," Proceedings of SPIE, Telemanipulator and Telepresence Technologies VI, vol. 3840, No. 234, Sep. 19, 1999, 14 pages.
Goldberg et al., "Collaborative Teleoperation via the Internet," IEEE International Conference on Robotics and Automation (ICRA), vol. 2, 2000, pp. 2019-2024.
Goldberg et al., "Desktop Teleoperation via the Word Wide Web," IEEE International Conference on Robotics and Automation, vol. 1, May 21-27, 1995, pp. 654-659.
Goldenberg et al., "Telemedicine in Otolaryngology," American Journal of Otolaryngology, vol. 23, No. 1, 2002, pp. 35-43.
Goldman, Lea, "Machine Dreams," available online at http://www.forbes.com/global/2002/0527/043.html, May 27, 2002, 5 pages.
Gostai, "Gostai Jazz, Robotic Telepresence," available online at http://www.robotshop.com/media/files/gostai-jass-information-sheet.pdf, 4 pages.
Gump, Michael D., Robot Technology Improves VA Pharmacies, U.S. Medicine Informational Central, Jul. 2001, 3 pages.
Han et al., "Construction of an Omnidirectional Mobile Robot Platform Based on Active Dual-Wheel Caster Mechanisms and Development of a Control Simulator," Journal of Intelligent and Robotic Systems, vol. 29, Issue 3, Nov. 2000, pp. 257-275.
Handley et al., "RFC 2327—SDP: Session Description Protocol," available online at http://www.faqs.org/rfcs/rfc2327.html, Apr. 1998, 22 pages.
Hanebeck et al., "ROMAN: A mobile Robotic Assistant for Indoor Service Applications," IEEE/RSJ International Conference on Intelligent Robots and Systems, vol. 2, Sep. 7-11, 1997, pp. 518-525.
Harmo et al., "Moving Eye-Interactive Telepresence Over Internet with a Ball Shaped Mobile Robot," available online at http://automation.tkk.fi/files/tervetaas/Moving_Eye4.pdf, 2000, 6 pages.
Haule et al., Control Scheme for Delayed Teleoperation Tasks, IEEE Pacific Rim Conference on Communications, Computers, and Signal Processing, May 17-19, 1995, pp. 157-160.
Hees, William P., "Communications Design for a Remote Presence Robot," CSCI E-131b, Final Project, Jan. 14, 2002, 12 pages.

(56) References Cited

OTHER PUBLICATIONS

Herias et al., "Flexible Virtual and Remote Laboratory for Teaching Robotics," Current Developments in Technology-Assisted Education, Jun. 2006, pp. 1959-1963.
Holmberg et al., Development of a Holonomic Mobile Robot for Mobile Manipulation Tasks, International Journal of Robotics Research, vol. 19, No. 11, Nov. 2000, pp. 1066-1074.
Ishiguro et al., "Integrating a Perceptual Information Infrastructure with Robotic Avatars: A Framework for Tele-Existence," IEEE-RSJ International Conference on Intelligent Robots and Systems, vol. 2, 1999, pp. 1032-1038.
Ishihara et al., "Intelligent Microrobot DDS (Drug Delivery System) Measured and Controlled by Ultrasonics," Intelligent Robots and Systems '91, Intelligence for Mechanical Systems, IEEE/RSJ International Workshop, vol. 2, Nov. 3-5, 1991, pp. 1145-1150.
ITU, "Call Completion Supplementary Services for H.323," ITU-T, Telecommunication Standardization Sector of ITU, H.450.9, Series H: Audiovisual and Multimedia Systems, Nov. 2000, 63 pages.
ITU, "Call Intrusion Supplementary Services for H.323," ITU-T, Telecommunication Standardization Sector of ITU, H.450.11, Series H: Audiovisual and Multimedia Systems, Mar. 2001, 59 pages.
ITU, "Packet-Based Multimedia Communications System," ITU-T, Telecommunication Standardization Sector of ITU, H.323, Series H: Audiovisual and Multimedia Systems, Feb. 1998, 128 pages.
ITU, "Transmission of Non-Telephone Signals: A Far End Camera Control Protocol for Videoconferences Using H.224," ITU-T, Telecommunication Standardization Sector of ITU, H.281, Nov. 1994, 12 pages.
Ivanov, Natali, "Master's Thesis: Internet Based Interface for Control of a Mobile Robot," Department of Numerical Analysis and Computer Science, 2003, 59 pages.
Jacobs et al., "Applying Telemedicine to Outpatient Physical Therapy," AMIA, Annual Symposium Proceedings, 2002, 1 page.
Jenkins et al., "Telehealth Advancing Nursing Practice," Nursing Outlook, vol. 49, No. 2, Mar. 2001, pp. 100-105.
Johanson, Mathias, "Supporting Video-Mediated Communication Over the Internet," Department of Computer Engineering, Chalmers University of Technology, Gothenburg, Sweden, 2003, 222 pages.
Jouppi et al., "BiReality: Mutually-Immersive Telepresence," Proceedings of the 12$^{th}$ Annual ACM International Conference on Multimedia, Oct. 10-16, 2004, pp. 860-867.
Jouppi et al., "First Steps Towards Mutually-Immersive Mobile Telepresence," Proceedings of the 2002 ACM Conference on Computer Supported Cooperative Work, Nov. 16-20, 2002, pp. 354-363.
Kanehira et al., "Virtual Humanoid Robot Platform to Develop Controllers of Real Humanoid Robots without Porting," IEEE/RSJ International Conference on Intelligent Robots and Systems, vol. 2, 2001, pp. 1093-1099.
Kaplan et al., "An Internet Accessible Telepresence," Multimedia Systems Journal, vol. 5, 1996, 7 pages.
Keller et al., "Raven Interface Project," The National Aviary's Teleconferencing Carnegie Mellon University Robot, Interaction and Visual Interface Design, School of Design, Carnegie Mellon University, 2001, 8 pages.
Khatib et al.,"Robots in Human Environments," Proceedings International Conference on Contrail, Automation, Robotics, and Vision ICRACV2000, 1999, 15 pages.
Knight et al., "Active Visual Alignment of a Mobile Stereo Camera Platform," IEEE International Conference on Robotics and Automation, vol. 4, Apr. 24-28, 2000, pp. 3203-3208.
Koenen, Rob, "MPEG-4: a Powerful Standard for Use in Web and Television Environments," (KPN Research), available online at http://www.w3.org/Architecture/1998/06/Workshop/paper26, July 1,2998, 4 pages.
Kurlowicz et al., Can the GestureCAM Be a Surrogate? Proceedings of the fourth European Conference on Computer-Supported Cooperative Work, 1995, pp. 181-196.
Kuzuoka et al., "Can The GestureCam Be a Surrogate?" Proceedings of the Fourth European Conference on Computer-Supported Cooperative Work, 1995, pp. 181-196.

Lane, Earl, "Automated Aides," Available online at http://222.cs.com.edu/nursebot/web/press/nd4380.htm, Oct. 17, 2000, 4 pages.
Lee et al., "A Novel Method of Surgical Instruction: International Telementoring," World Journal of Urology, vol. 16, No. 6, Dec. 1998, pp. 367-370.
Leifer et al., "VIPRR: A Virtually In Person Rehabilitation Robot," Proceedings of 1997 International Conference on Rehabilitation Robotics, Apr. 14-15, 1997, 4 pages.
Lemaire, Edward, "Using Communication Technology to Enhance Rehabilitation Services: A Solution Oriented User Manual," Institute of Rehabilitation Research and Development, Terry Fox Mobile Clinic, The Rehabilitation Centre, Ottawa, Ontario, Canada, Version 2.0, available online at http://www.irrd.ca/telehealth/distfile/distman_v2_1.pdf, 1998-2001, 104 pages.
Library of Congress, "008-Fixed-Length Data Elements (NR)," MARC 21 Format for Classification Data, available online at http://loc.gov/marc/classification/cd008.html, Jan. 2000, pp. 1-14.
Lim et al., "Control to Realize Human-Like Walking of a Biped Humanoid Robot," IEEE International Conference on Systems, Man, and Cybernetics, 2000, vol. 5, 2000, pp. 3271-3276.
Linebarger et al., "Concurrency Control Mechanisms for Closely Coupled Collaboration in Multithreaded Virtual Environments," Department of Computer Science and Engineering, Lehigh University, vol. 13, 2004, 40 pages.
Long, William F., "Robot Navigation Technology," available online at http://www.atp.nist.gov/eao/sp950-1/helpmate.htm, Mar. 1999, 3 pages.
Luna, Nancy, "Robot a New Face on Geriatric Care," OCREGISTER.com, Aug. 6, 2003, 3 pages.
Mack, Michael J., "Minimally Invasive and Robotic Surgery," The Journal of the American Medical Association, vol. 285, No. 5, 2001, pp. 568-572.
Mair, G.M., "Telepresence—The Technology and its Economic and Social Implications," Technology and Soceity, 1997, Technology and Society at a Time of Sweeping Change, Proceedings, 1997, International Symposium, Jun. 20-21, 1997, pp. 118-124.
Martin, Anya, "Brighter Days Ahead," Assisted Living Today, vol. 9, Nov./Dec. 2002, pp. 19-22.
McCardle et al., "The Challenge of Utilizing New Technology in Design Education," Loughborough University, IDATER 2000, 2000, pp. 122-127.
Meng et al., "E-Service Robot in Home Healthcare," Proceedings of the 2000 IEEE-RSJ, International Conference on Intelligent Robots and Systems, 2000, pp. 832-837.
Metz, Cade, "HP Labs," available online at http://www.pcmag.com/article2/0,2817,1130820,00.asp, July 1, 2003, 4 pages.
Michaud, Anne, "Introducing Nursebot," available online at http://www.cs.cmu.edu/nursebot/web/press/globe_301/index.html, 2001, 4 pages.
Microsoft Corporation, Inc. "Microsoft NetMeeting 3 Features excerpt from Official Microsoft NetMeeting 3.0 Book," available online at http://technet.microsoft.com/en-us/library/cc723477.aspx, 2012, 6 pages.
Minsky, Marvin, "Telepresence," OMNI Magazine, Jun. 1980, 6 pages.
Montemerlo, Reddy Whittaker, "Telepresence: Experiments in Next Generation Internet," available online at http://www.ri.cmu.edu/creative/archives.htm. Oct. 20, 1998, 3 pages.
Murphy, Robin R., "Introduction to A1 Robotics," A Bradford Book, The MIT Press, Cambridge Massachusetts, London, England, 2000, 487 pages.
Nakajima et al., "A Multimedia Teleteaching System Using an Electronic Whiteboard for Two Way Communication of Motion Videos and Chalkboards," 2$^{nd}$ IEEE International Workshop on Robot and Human Communication, 1993, pp. 436-441.
Nakazato et al., "Group-Based Interface for Content-Based Image Retrieval," Proceedings of the Working Conference on Advanced Visual Interfaces, 2002, pp. 187-194.
Nakazato et al., "ImageGrouper: A Group-Oriented User Interface for Content-Based Image Retrieval and Digital Image Arrangement," Journal of Visual Languages & Computing, vol. 14, No. 4, Aug. 2003, pp. 45-46.

(56) References Cited

OTHER PUBLICATIONS

Nersc, "Berkeley Lab's RAGE Telepresence Robot Captures R&D 100 Award," Available online at http://www.nersc.gov/news-publications/news/nersc-center-news/2002/berkeley-lab-s-raqe-telepresence-robot-captures-r-and-d100-award/, Jul. 2, 2002, 2 pages.
Nomadic Technologies Inc., "Nomad XR4000 Hardware Manual," Release 1.0, Mar. 1999, 34 pages.
Noritsugu et al., "Application of Rubber Artificial Muscle Manipulator as a Rehabilitation Robot," Mechatronics, IEEE/ASME Transactions, vol. 2, No. 4, Dec. 1997, pp. 259-267.
North, Michael, "Telemedicine: Sample Script and Specifications for a Demonstration of Simple Medical Diagnosis and Treatment Using Live Two-Way Video on a Computer Network," Greenstar Corporation, 1998, 5 pages.
Office Action received for Chinese Patent Application No. 200680044698.0 dated Nov. 4, 2010, 26 pages.
Ogata et al., "Development of Emotional Communication Robot: WAMOEBA-2R—Experimental Evaluation," Proceedings of the 2000 IEEE/RSJ International Conference on Intelligent Robots and Systems, vol. 1, 2000, pp. 175-180.
Ogata et al., "Emotional Communication Robot: WAMOEBA-2R—Emotion Model and Evaluation Experiments," Proceedings of the International Conference on Humanoid Robots, 2000, pp. 1-16.
Oh et al., "Autonomous Battery Recharging for Indoor Mobile Robots," Proceedings of Australian Conference on Robotics and Automation, 2000, pp. 1-6.
Ojha, Anand K., "An Application of Virtual Reality in Rehabilitation," Proceedings of the 1994 IEEE Southeastcon 94. Creative Technology Transfer—A Global Affair, Apr. 1994, pp. 4-6.
Opening Brief for Plaintiff-Appellant InTouch Technologies, Inc., Appeal from the U.S. District Court for the Central District of California in Case No. 11-cv-9185, Judge Percy Anderson, Apr. 12, 2013, 187 pages.
Osborn, Jim, "Quality of Life Technology Center," QoLT Research Overview: A National Science Foundation Engineering Research Center, Carnegie Mellon University of Pittsburgh, 2 pages.
Panusopone et al., "Performance Comparison of MPEG-4 and H.263+ for Streaming Video Applications," Circuits Systems Signal Processing, vol. 20, No. 3, 2001, pp. 293-309.
Paulos et al., "A World Wide Web Telerobotic Remote Environment Browser," Available online at http://www.w3.org/Conferences/WWW4/Papers/326/, 1995, 15 pages.
Paulos et al., "Designing Personal Tele-Embodiment," Proceedings of IEEE International Conference on Robotics and Automation, vol. 4, May 16-20, 1998, pp. 3173-3178.
Paulos et al., "Personal Tele-Embodiment," Chapter 9 in Goldberg, et al., ed. "Beyond Webcams," MIT Press, Jan. 4, 2002, pp. 155-167.
Paulos et al., "PRoP: Personal Roving Presence," ACM:CHI Proceedings of CHI '98, 1998, 8 pages.
Paulos et al., "Social Tele-Embodiment: Understanding Presence," Autonomous Robots, vol. 11, Issue 1, Kluwer Academic Publishers, Jul. 2001, pp. 87-95.
Paulos et al., "Ubiquitous Tele-Embodiment: Applications and Implications," International Journal of Human Computer Studies, vol. 46, No. 6, Jun. 1997, pp. 861-877.
Paulos, Eric J., "Personal Tele-Embodiment," Dissertation, Doctor of Philosophy in Computer Science in the Graduate Division of the University of California at Berkeley, 2001, 282 pages.
Paulos, Eric John Canny, "Video of PRoP 2 at Richmond Field Station," www.prop.org Printout of Home Page of Website and two-page transcript of the audio portion of said PRoP Video, May 2001, 2 pages.
Paulos, Eric John, "Personal Tele-Embodiment," Introductory and cover pages from 2201 Dissertation including Contents table, together with emails relating thereto from UC Berkeley Libraries, as shelved at UC Berkeley Engineering Library (Northern Regional Library Facility), May 8, 2002, 25 pages (including 4 pages of emails).
Paulos, Eric John, "Personal Tele-Embodiment," OskiCat Catalog Record, UCB Library Catalog, 2001,3 pages.
PictureTel Adds New Features and Functionality To Its Award-Winning Live200 Desktop Videoconferencing System, PR Newswire Association, LLC, Gale, Cengage Learning, Jun. 13, 1997, 5 pages.
Picturetel Corporation, "PictureTel Live200 for Windows NT Product Guide," 1997, 63 pages.
Pin et al., "A New Family of Omnidirectional and Holonomic Wheeled Platforms for Mobile Robots," IEEE Transactions on Robotics and Automation, vol. 10, No. 4, Aug. 1994, pp. 480-489.
Piquepaille, Roland, "This Blog and its RSS Feed are Moving," Roland Piquepaille's Technology Trends, How new technologies are modifying our way of life, Oct. 31, 2004, 2 pages.
Radvision, "Making Sense of Bandwidth the Netsense Way," Network Congestion in Unmanaged networks Bandwidth Estimation and Adaptation Techniques, White Paper, Radvision's Netsense Technology, 2010, 7 pages.
Reply Brief for Defendant-Appellee VGO Communications, Inc., Appeal from the U.S. District Court for the Central District of California, in Case No. 2:11-cv-9185, Judge Percy Anderson, May 28, 2013, 75 pages.
Reply Brief for Plaintiff-Appellant InTouch Technologies, Inc., Appeal from the U.S. District Court for the Central District of California, in Case No. 11-cv-9185, Judge Percy Anderson, Jun. 14, 2013, 39 pages.
Reynolds et al., "Review of Robotic Telemedicine Utilization in Intensive Care Units (ICUs)," 11$^{th}$ Annual ATA Symposium, Tampa, Florida, 2011, 1 page.
Roach, Adam, "Automatic Call back Service in SIP," Internet Engineering Task Force, Internet Draft, Category: Informational, Mar. 2000, 8 pages.
Rovetta et al., "A New Telerobotic Application: Remote Laparaoscopic Surgery Using Satellites and Optical Fiber Networks for Data Exchange," International Journal of Robotics Research, vol. 15, No. 3, Jun. 1, 1996, pp. 267-279.
Roy et al., "Towards Personal Service Robots for the Elderly," Workshop on Interactive Robots and Entertainment (WIRE 2000), available online at <http:www.ri.cmu.edu/pb_files/pub2/roy_nicholas_2000_1.pdf>, vol. 25, Apr. 30-May 1, 2000, 7 pages.
Sachs et al., "Virtual Visit: Improving Communication for Those Who Need it Must," Studies in Health Technology asn Informatics, vol. 94, Medicine Meets Virtual Reality 11, 2003, pp. 302-308.
Salemi et al., "MILO: Personal Robot Platform," IEEE-RSJ International Conference on Intelligent Robots and Systems, Aug. 2005, pp. 4089-4094.
Sandt et al., "Perceptions for a Transport Robot in Public Environments," Proceedings of the 1997 IEEE/RSJ International Conference on Intelligent Robots and Systems, vol. 1, Sep. 7-11, 1997, pp. 360-365.
Sawyer, Robert J., "Inventing the Future: 2000 years of Discovery," available online at http://www.sfwriter.com/pritf.htm, Jan. 2, 2000, 2 pages.
Schaeffer et al., "Care-O-BotTM: The Concept of a System for Assisting Elderly or Disabled Persons in Home Enviornments," Proceedings of the 24$^{th}$ Annual Conference of the IEEE Industrial Electronics Society, vol. 4, 1998, pp. 2476-2481.
Schraft et al., "Care-O-bot™: The Concept of a System for Assisting Elderly or Disabled Persons in Home Environments," IEEE Proceedings of the 24th Annual Conference of the Industrial Electronics Society, IECON '98, Aug. 31-Sep. 4, 1998, pp. 2476-2481.
Schultz et al., "Web Interfaces for Mobile Robots in Public Places," IEEE Robotics & Automation Magazine, vol. 7, No. 1, Mar. 2000, pp. 48-56.
Screenshot Showing Google Date for Lemaire Telehealh Manual, screenshot retrieved on Dec. 18, 2014, 1 page.
Shimoga et al., "Touch and Force Reflection for Telepresence Surgery," Proceedings of the 16$^{th}$ Annual International Conference of the IEEE Engineering in Medicine and Biology Society, Nov. 1994, pp. 1049-1050.
Siegwart et al., "Interacting Mobile Robots on the Web," Proceedings of the 1999 IEEE International Conference on Robotics and Automation, May 1999, pp. 1-7.
Simmons et al., "Xavier: An Autonomous Mobile Robot on the Web," IEEE Robotics and Automation Magazine 1999, pp. 43-48.

(56) References Cited

OTHER PUBLICATIONS

Stephenson, Gary, "Dr. Robot Tested at Hopkins," available online at http://www.hopkinsmedicine.org/press/2003/august/030805.htm, Aug. 5, 2003, 2 pages.
Stoianovici et al., "Robotic Tools for Minimally Invasive Urologic Surgery," Complications of Urologic Laparoscopic Surgery: Recognition, Management and Prevention, Dec. 2002, 17 pages.
Suplee, Curt, "Mastering the Robot," The Washington Post, Washington Post Staff Writer, Sep. 17, 2000, 5 pages.
Tahboub et al., "Dynamics Analysis and Control of a Holonomic Vehicle with Continuously Variable Transmission," Transactions of the ASME, Journal of Dynamic Systems, Measurement and Control, vol. 124, Mar. 2002, pp. 118-126.
Telepresence Research, Inc., "The Telepresence Mobile Robot System," available online at http://www.telepresence.com/telepresence-research/TELEROBOT/, Feb. 20, 1995, 3 pages.
Tendick et al., "Human-Machine Interfaces for Minimally Invasive Surgery," Proceedings of the 19th Annual International Conference of the IEEE Engineering in Medicine and Biology Socieity, Oct. 30-Nov. 2, 1997, pp. 2771-2776.
Theodosiou et al., MuLVAT: A Video Annotation Tool Based on XML-Dictionaries and Shot Clustering, 19th International Conference, Artificial Neural Networks—ICANN 2009, Part II, Sep. 14-17, 2009, pp. 913-922.
Thrun et al., "Probabilistic Algorithms and the Interactive Museum Tour-Guide Robot Minerva," International Journal of Robotics Research, vol. 19, 20000, pp. 1-35.
Time, Lists, "Office Coworker Robot," Bestr Inventions of 2001, available online at http://content.time.com/time/specials/packages/article/0,28804,1936165_1936255_1936640,00.html, Nov. 19, 2001, 2 pages.
Tipsuwan et al., "Gain Adaptation of Networked Mobile Robot to Compensate QoS Deterioration," 28th Annual Conference of the Industrial Electronics Society, vol. 4, Nov. 5-8, 2002, pp. 3146-3151.
Tsui et al., "Exploring Use Cases for Telepresence Robots," 6th ACM/IEEE International Conference on Human-Robot Interaction (HRI), Mar. 2011, pp. 11-18.
Tyrrell et al., "Teleconsultation in Psychology: The Use of Videolinks for Interviewing and Assessing Elderly Patients," Age and Ageing, vol. 30, No. 3, May 2001, pp. 191-195.
Tzafestas et al., "VR-Based Teleoperation of a Mobile Robotic Assistant: Progress Report," Technical Report DEMO 2000/13, Institute of Informatics and Telecommunications, National Center for Scientific Research "Demokritos," Nov. 2000, pp. 1-23.
Umass Lowell Robotics Lab, "Robotics Lab @ UMASS Lowell," Borchure, 2011, 2 pages.
Urquhart, Kim, "InTouch's Robotic Companion 'Beams Up' Healthcare experts," Medical Device Daily, vol. 7, No. 39, Feb. 27, 2003, pp. 1,4.
U.S. Appl. No. 10/783,760, filed Feb. 20, 2004, 48 pages.
U.S. Appl. No. 60/449,762, filed Feb. 24, 2003, 28 pages.
Using Your Infrared Cell Phone Camera, available online at http://www.calsdomain.com/xray/about.htm, Courtesy of Internet Wayback Machine, Jan. 30, 2010, 4 pages.
Video Middleware Cookbook, "H.350 Directory Services for Multimedia," 2 pages.
Weaver et al., "Monitoring and Controlling Using the Internet and Java," Proceedings of the 25th Annual Conference of the IEEE Industrial Electronics Society, vol. 3, 1999, pp. 1152-1158.
Weiss et al., "PEBBLES: A Personal Technology for Meeting Education, Social and Emotional Needs of Hospitalised Children," Personal and Ubiquitous Computing, vol. 5, No. 3, Aug. 2001, pp. 157-168.
Weiss et al., "Telework and Video-Mediated Communication: Importance of Real-Time, Interactive Communication for Workers with Disabilities," available online at http://www.telbotics.com/research_3.htm retrieved on Nov. 23, 2010, 3 pages.
West et al., "Design of Ball Wheel Mechanisms for Omnidirectional Vehicles with Full Mobility and Invariant Kinematics," Journal of Mechanical Design, vol. 119, Jun. 1997, pp. 153-161.
Yamasaki et al., "Applying Personal Robots and Active Interface to Video Conference Systems," 6th International Conference on Human Computer Interaction, vol. B, 1995, pp. 243-248.
Yamauchi, Brian, "PackBot: A Versatile Platform for Military Robotics," Proceedings of SPIE for Military Robotics, 2004, pp. 228-237.
Yong et al., "Robot Task Execution with Telepresence Using Virtual Reality Technology," 1998 International Conference on Mechatronic Technology, Nov. 30-Dec. 2, 1998, pp. 1-8.
Zambroski, James, "CMU, Pitt Developing Nursebot," available online at http://www.cs.cmu.edu/~nursebot/web/press/tribunereview.html, Oct. 27, 2000, 3 pages.
Zamrazil, Kristie, "Telemedicine in Texas: Public Policy Concerns," Focus Report, House Research Organization, Texas House of Representatives, No. 76-22, May 5, 2000, pp. 1-16.
Zipperer, Lorri, "Robotic Dispensing System," ISMP Medical Safety Alert!, vol. 4, No. 17, Aug. 25, 1999, 2 pages.
Zorn, Benjamin G., "Ubiquitous Telepresence," Department of Computer Science, University of Colorado, 1996, 13 pages.
Nomad Scout User's Manual, Nomadic Technologies, Software Version 2.7, Part No. DOC00004, Jul. 12, 1999, pp. 1-59.

\* cited by examiner

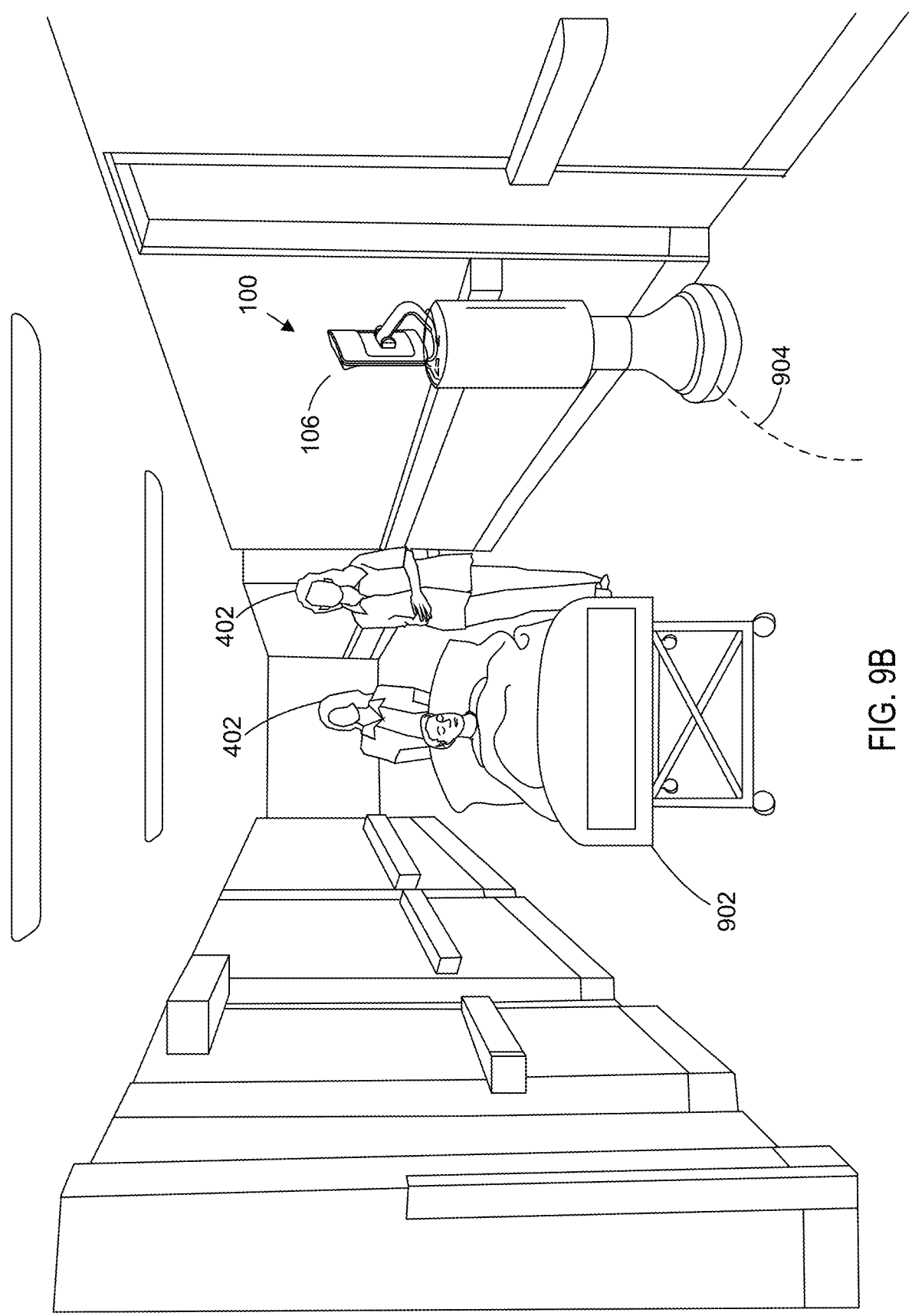

SOCIAL BEHAVIOR RULES FOR A MEDICAL TELEPRESENCE ROBOT

RELATED APPLICATIONS

This application is a continuation of U.S. patent application Ser. No. 16/418,605, filed May 21, 2019, for "Social Behavior Rules fora Medical Telepresence Robot," which is a continuation of U.S. patent application Ser. No. 15/720, 214, filed Sep. 29, 2017, for "Social Behavior Rules fora Medical Telepresence Robot," which is continuation of U.S. patent application Ser. No. 14/931,641, filed, Nov. 3, 2015, for "Social Behavior Rules fora Medical Telepresence Robot," which is a continuation of U.S. patent application Ser. No. 14/550,743, filed Nov. 21, 2014, for "Social Behavioral Rules for a Medical Telepresence Robot," now U.S. Pat. No. 9,174,342, which is a continuation of PCT Application No. PCT/US2013/031778, for "Social Behavioral Rules for a Medical Telepresence Robot," filed Mar. 14, 2013. The forgoing applications also claim priority under 35 U.S.C. § 119(e) to U.S. Provisional Application No. 61/650, 205 filed May 22, 2012, titled "Remote Presence Interface and Patient Data Integration"; U.S. Provisional Application No. 61/674,794 filed Jul. 23, 2012, titled "Graphical User Interfaces Including Touchpad Driving Interfaces for Telemedicine Devices"; U.S. Provisional Application No. 61/674,796 filed Jul. 23, 2012, titled "Clinical Workflows Utilizing Autonomous and Semi-Autonomous Telemedicine Devices"; U.S. Provisional Application No. 61/674,782 filed Jul. 23, 2012, titled "Behavioral Rules For a Telemedicine Robot To Comply With Social Protocols"; and U.S. Provisional Application No. 61/766,623 filed Feb. 19, 2013, titled "Graphical User Interfaces Including Touchpad Driving Interfaces for Telemedicine Devices." All of the foregoing applications are all hereby incorporated by reference in their entireties.

TECHNICAL FIELD

This disclosure is generally related to behaviors and actions that can be executed by an autonomous or semi-autonomous robot to appear more human-like and/or comply with social protocols.

BRIEF DESCRIPTION OF THE DRAWINGS

FIG. 9B is a perspective view of a robot allowing the large group of FIG. 9A to pass with a head portion rotated.

DETAILED DESCRIPTION

In order to improve communication among hospital staff, healthcare professionals, patients, and other applicable parties in various locations, a robot may serve as a remote presence communication device. The robot may be capable of autonomous or semi-autonomous navigation through a healthcare facility with little or no manual intervention. The robot may drive in a manner such that it avoids both stationary and moving obstacles and people in its path.

In addition to avoiding contact with obstacles and people, the robot may move in harmony with social protocols and expectations. For example, this may include providing suitable space between itself and people, as well as moving in an unobtrusive manner so as not to alarm staff or visitors. Further, the robot may move fluidly within that context. The robot may also be capable of acting as a member of a group, enabling it to assist in group activities and procedures within a healthcare facility environment.

Disclosed herein are various embodiments of robots, robot behaviors, and methods for robots to achieve the various behaviors. According to various embodiments, the systems and methods disclosed herein may facilitate communication among medical professionals, staff, and patients. In addition, the systems and methods described herein facilitate the autonomous navigation of robots while engaging in human behaviors and obeying social protocols. For example, a doctor in a remote location may cause a robot to drive down a hallway to a patient's room. As the robot autonomously navigates to the patient's room, the robot may acknowledge and greet a human as it passes en route to a patient room.

Figure 1:
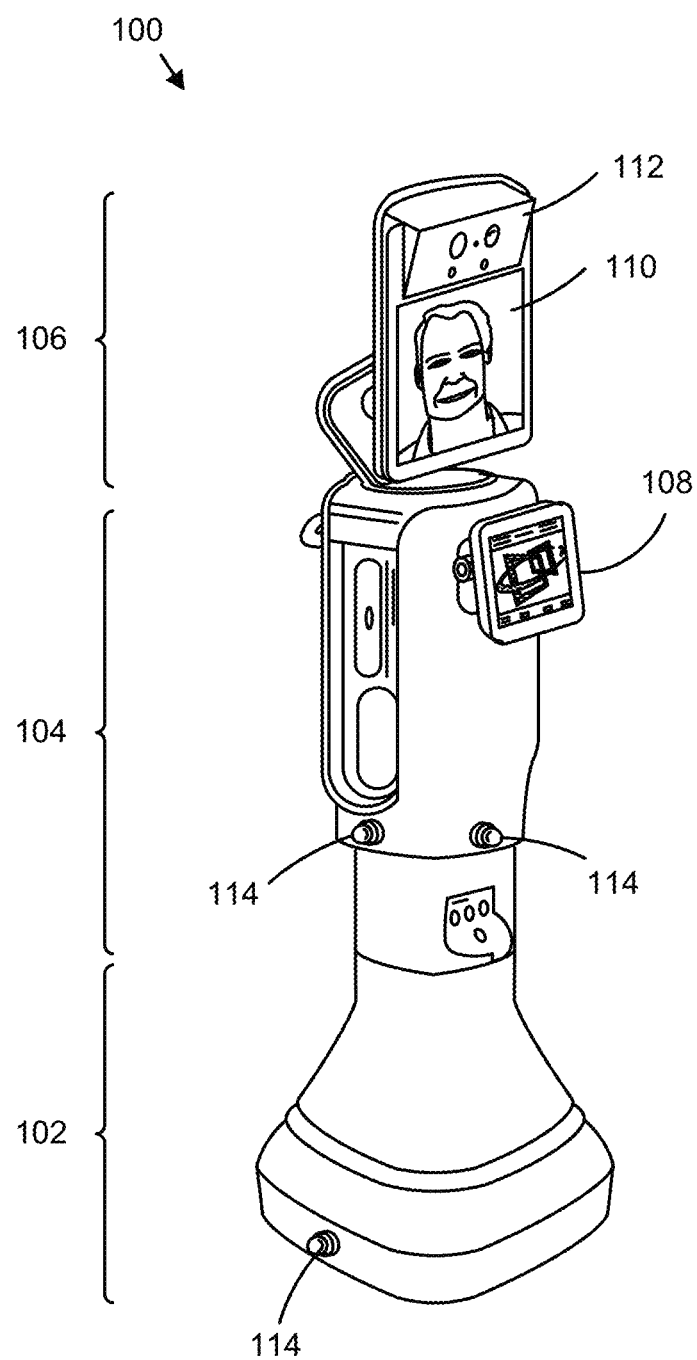
FIG. 1 is a perspective view of a medical telepresence robot.

FIG. 1 is a perspective view of a telepresence robot 100, according to one embodiment. The robot 100 includes a base 102, an upper portion 104, and a head 106. The robot 100 provides a variety of features and functions for allowing a user to remotely control the robot 100 and communicate with individuals on the site of the robot 100. For example, a doctor may be able to use the robot 100 to remotely communicate with a patient or coworker.

The base 102 supports the robot 100 and may include a drive system for moving the robot 100 about a work area. The base 102 may include any associated motors, batteries, wheels, or the like to move the robot 100. The upper portion 104 supports the head 106 and houses various component of the robot 100. The upper portion 104 may also provide various features and interfaces to allow a person to interface with the robot 100. For example, the upper portion 104 includes a display interface 108 that displays information about the robot 100 and/or allows a user to select different options to control the robot 100. Other ports, button, lights, or the like may be used to interface with the robot 100. In one embodiment, the upper portion 104 is configured to rotate independently of the base 102.

The head 106 represents a head of the robot 100 and includes a display screen 110 and a sensor housing 112. The display screen 110 may be used to selectively display video of a remote user, a caricature corresponding to a personality of the robot 100, or any other information. The display screen 110 may be configured to display a live video feed from a remote operator and/or a persona of the robot 100, itself. For example, the display screen 110 may display the face of a doctor remotely using the robot 100 for teleconsultations. When autonomously navigating, the robot 100 may have a personality portrayed through a caricature, face, icon, or other characteristic on the display screen 110.

The sensor housing 112 may house a variety of sensors such as microphones, cameras, range detector devices, or the like. For example, a video camera configured to capture a video feed of a point of view of the robot 100 may be captured and transmitted to a remote user. The video camera may also be used in conjunction with a range finding device, such as a laser range finder, to detect objects, humans, or other surrounding features that affect navigation of the robot 100. In one embodiment, the head 106 is able to rotate independently of the upper portion 104 and/or the base 102. In another embodiment, the head 106 is not rotatable with respect to the upper portion 104 and/or the base 102.

The robot 100 also includes lights 114 distributed on the surface of the robot 100. The lights 114 may be used to indicate a current status of the robot 100, reflect a personality of the robot 100, indicate an emergency, create a desired mood for a location within a work area, or indicate any other information to nearby humans. The robot 100 may also include additional lights, input devices, output devices, and/or a variety of other sensors that will be discussed below.

Figure 2:
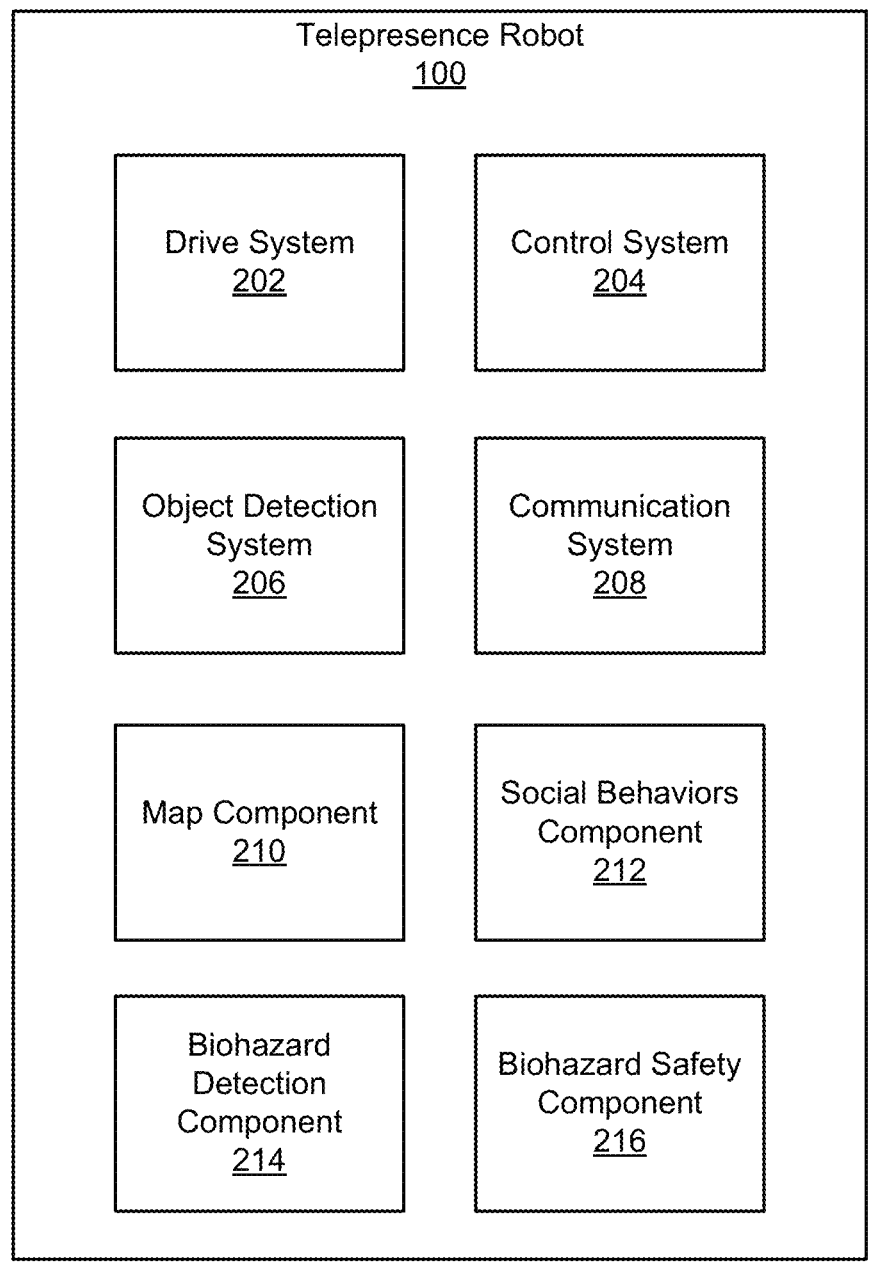
FIG. 2 is a schematic block diagram illustrating example components of the telepresence robot of FIG. 1.

FIG. 2 is a schematic block diagram illustrating example components of the robot 100 of FIG. 1. In the depicted embodiment, the robot 100 includes a drive system 202, a control system 204, an object detection system 206, a communication system 208, a map component 210, a social behaviors component 212, a biohazard detection component 214, and a biohazard safety component 216. The components 202, 204, 206, 208, 210, 212, 214, and 216 are provided by way of example only and may not be included in all embodiments. For example, various embodiments may include any one or any combination of two or more of the components 202, 204, 206, 208, 210, 212, 214, and 216, without limitation.

The drive system 202 may include one or more motors, wheels, or other hardware to move the robot 100. The drive system 202 may be configured for navigation on a variety of surfaces such as concrete, linoleum, carpet, or the like. In one embodiment, the drive system 202 is configured to provide traction and the ability to move through many of the environments found in a hospital. In one embodiment, the drive system 202 is an omnidirectional drive system that allows the robot 100 to move in any direction.

The control system 204 is configured to control the robot 100. The control system 204 may receive input from the various other components, such as components 202, 206, 208, 210, 212, 214, and 216, and generate instructions to move or otherwise control the robot based on the input. For example, the control system 204 may be configured to control the drive system 202 to navigate the robot 100 around a work area.

The control system 204 may be configured to control the robot 100 according to a variety of different operating modes. In one embodiment, the control system 204 is configured to operate the robot 100 according to an autonomous mode. In the autonomous mode, the control system 204 may control the robot 100 to navigate and perform a variety of tasks with no human input. For example, the control system 204 may cause the robot 100 to navigate through a work area and/or perform tasks without human input.

In one embodiment, the control system 204 may cause the robot to perform tasks it is capable of performing on its own and request help from a human when needed. For example, the robot 100 may be configured to open closed doors, request help with closed doors, and/or wait for a closed door to be opened. For example, automatic doors may be opened by the robot 100. The robot 100 may include a key fob or other identifying tag or information to open secure access doors. The robot 100 may be configured to monitor for people following it through secure areas and provide an appropriate alert. In some embodiments, the robot 100 may wait patiently for a door to open or actively request assistance from nearby humans. The robot 100 may have a time out period after which it may find a new path that does not require the door to be opened. Alternatively, the robot may wait patiently for a predetermined amount of time, after which it may begin requesting help. In some embodiments, the robot 100 may track statistics associated with the amount of time it waits or receives help at each door and utilize the information during route planning.

The robot 100 may be configured to proactively request human help if it is presented with a situation that it is not programmed to respond to. The robot 100 may request help via various methods, such as sending an SMS or other electronic message, using its display interface 108 to communicate its need for assistance, or utilizing other communication methods. In some embodiments, a remote operator can be summoned for manual assistance with the situation, allowing the robot 100 to reassert its autonomy.

In a semi-autonomous mode, the control system 204 may receive instructions from a user and then operate autonomously to accomplish the instructions. For example, a user may provide an instruction to navigate to a specific patient room. The control system 204 may then navigate to the patient room autonomously, accounting for objects, individuals, routes, or other information to arrive at the room in a timely and safe manner. The control system 204 may receive input from the other components 202, 206, 208, 210, 212, 214, and 216 to navigate in a social and safe manner.

In a manual mode, the control system 204 may perform instructions as provided by a user. For example, a user may remotely drive the robot 100 using a joystick or other input device or method and the control system 204 may cause the drive system 202 to move the robot 100 in the manner defined by the user. Of course, some aspects of the operation of the robot 100 may still be automated and may not require explicit instruction from a user. In any of the manual, semi-autonomous, or autonomous modes, a user may be able to remotely operate (or tele-operate) and/or view information provided by the robot 100.

According to one embodiment, changes in operation mode may be accompanied by variations in restrictions on the operation of the robot 100. For example, the robot's maximum allowed speed in a manual mode may be increased, and the remote user may be able to navigate the robot 100 into regions from which the robot 100 may be locked out in an autonomous mode. In another embodiment, the remote user may be able to override obstacle avoidance to approach people or obstacles closely, or even touch them. This may be specifically useful during teleoperated consultations, such as with a coworker, client, or patient.

With regard to humans present with the robot 100, the robot 100 may contain manual intervention functions such that a person may stop or delay the robot 100. These may be useful if the robot 100 is getting in the way of current events in the work area or to prevent accidents or other problems. In some embodiments, the display interface 108 may contain a large "stop" button, which when pressed may cause the robot 100 to halt motion and display a "resume" button. A person may thereby stop or delay the robot 100 until the person manually resume its motion, or until an internal timer sets the robot 100 back in motion. The robot 100 may also halt as a result of being manually shoved. In either case, the robot 100 may start an internal timer that will count down a pre-determined amount of time until the robot 100 resumes its course. In some embodiments, the display interface 108 may display a message that indicates how long before the robot 100 resumes motion. A person may have the option to set the robot 100 back into motion immediately by selecting a "resume" button, or to keep the robot 100 stopped by selecting a "remain stopped" button. In another embodiment, if the person selects the "remain stopped" button, the time the robot 100 is to remain halted will increase. The person may be able to select the "remain stopped" button a number of times to increase the halt time of the robot 100 up to a certain maximum time.

In other embodiments, the robot 100 may resume navigation and/or motion immediately after being shoved and/or a "stop" button is selected. In still other embodiments, the robot 100 may remain permanently stopped until further input is provided in response to a "stop" button being pushed and/or in response to a shove. The robot 100 may be configured to go into a freewheel mode when stopped, such that the robot 100 is able to be moved or shoved out of the way. In some embodiments, the robot 100 may selectively enter a freewheel mode depending on the surface it is on. For example, it may not enter a freewheel mode if it detects that it is on an inclined surface. When stopped, the robot 100 may include an "enter freewheel mode" selection on the display interface 108 that may be selected to cause the robot 100 to enter the freewheel mode. A person present with the robot 100 may thereby be able to position the robot 100 in a location out of the way of a current procedure or event.

The object detection system 206 may detect the presence of an object, human, or other physical feature that is near the robot 100. The object detection system 206 may be used by the robot 100 to detect three-dimensional information about its environment and may provide this information to the control system 204 or other component to affect navigation of the robot 100. The object detection system 206 may use a variety of sensors, cameras, or other devices to detect information about the environment of the robot 100. For example, the robot 100 may include stereo cameras, a laser range finder, a radar system, a sonar system, and/or any other system for observing and/or detecting objects or features nearby.

The object detection system 206 may use any of a wide variety of known system and methods of motion detection, facial recognition techniques, and/or other detection algorithms to detect individuals and/or objects. For example, a robot or related system may utilize binary pattern-classification techniques, Viola-Jones object detection frameworks, speeded up robust features (SURF) as local descriptors for facial recognition and detection, edge matching (e.g., Canny edge detection), greyscale matching, gradient matching, histograms of receptive field responses, scale invariant feature transforms (SIFTs), and other techniques known in the art. Such techniques may also be fused with face-detection and/or used in combination.

The object detection system 206 may be configured to discern a human from other objects using any of the above methods and may further use motion detection, face detection, feature classification for body shapes, and/or other suitable techniques. The object detection system 206 may also be used to detect a type of object. For example, using methods such as SIFT-based object detection, the robot 100 may identify objects such as beds, chairs, carts on wheels, intravenous (IV) poles, open drawers, or other common objects.

The communication system 208 may be used to provide communication to and from the robot 100 to other devices and remote users. The communication system 208 may allow the robot 100 to communicate wirelessly with a control center, remote user, on-site workers or staff, or the like. The communication system 208 may allow instructions to be sent to the robot 100 and may allow the robot to provide information regarding its current location, status, or other information. For example, the communication system 208 may provide a captured video feed to a remote client and may receive a client video feed of a user at the remote client. The client video feed may be displayed on the display screen 110 for viewing by local humans.

The map component 210 may determine a location of the robot 100 within the work area. For example, the robot 100 may have access to maps for a healthcare facility or other work area. In one embodiment, the robot 100 may maintain, create, and/or download maps of its work area. The maps may be annotated and/or marked with various features and/or describe how the robot 100 should behave in various zones or regions. The map may include various areas that are off limits as well. Some regions or areas of a healthcare facility, hospital, or other work area may be unmapped. In some embodiments, the robot 100 should avoid and/or be restricted from unmapped areas. In some embodiments, the robot 100 may avoid unmapped areas in an autonomous mode, but allow for manual tele-operation within the unmapped regions. The robot 100 may be configured to warn a user when crossing a boundary between a mapped area and an unmapped area.

In one embodiment, map component 210 may be configured to map the unmapped areas as the robot 100 autonomously navigates or is tele-operated within unmapped areas. The robot may be configured to memorize a path within an unmapped area as it is operated in a manual or semi-manual mode sufficient for the robot 100 to retrace its path back to a mapped area. The robot 100 may then localize itself at the spot the robot 100 crossed the boundary.

The map component 210 may be able to determine where within a map the robot 100 is located. In some embodiments, the robot 100 may be configured to indicate locally (e.g., lights, audible warnings, a message on a display interface) or remotely (e.g., a wireless message) that it is lost when the map component 210 is unable to determine the location of the robot 100. A user may be alerted and help guide the robot 100 to a mapped region. The robot 100 may be guided locally, such as through a follow option described herein, or be tele-operated and manually driven to a mapped region.

Examples of mapping systems, tags, and robots, and interactions there between are described in U.S. patent application Ser. No. 13/360,579 filed on Jan. 27, 2012, titled "INTERFACING WITH A MOBILE TELEPRESENCE ROBOT," which application is hereby incorporated by reference in its entirety, and in U.S. patent application Ser. No. 13/360,590 filed on Jan. 27, 2012, titled "INTERFACING WITH A MOBILE TELEPRESENCE ROBOT," which application is hereby incorporated by reference in its entirety.

The social behaviors component 212 determines operations for the robot 100 to perform to operate according to social protocols to reduce anxiety or discomfort of nearby humans. For example, if a robot moves in an erratic manner or comes too close to nearby people, those people may be uncomfortable and may find the presence of the robot to make it harder to relax, move between locations, or go about their duties. The social behaviors component 212 may determine various actions for the robot 100 that allow the robot 100 to operate around others without being a distraction or causing problems. According to one embodiment, the social behaviors component 212 will determine actions or operations to be performed based on a detected status, environment, or individual. The social behaviors component 212 may cause the robot 100 to operate differently based on the detected status, environment, or individual.

Figure 3:
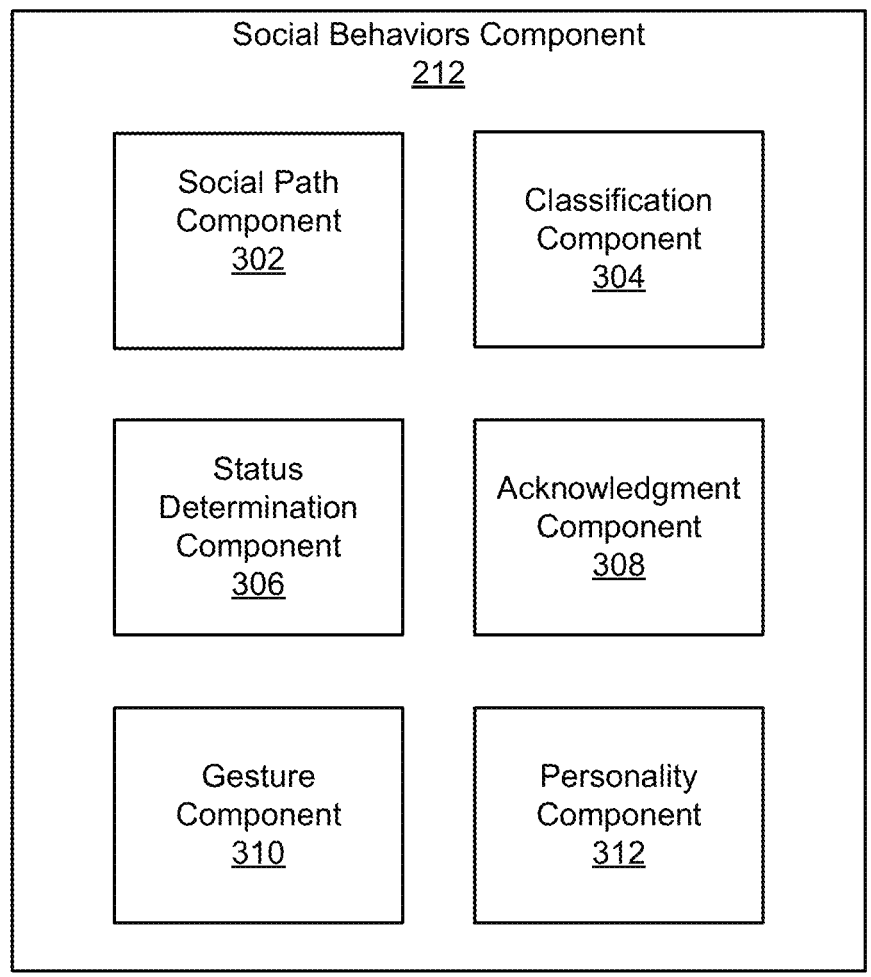
FIG. 3 is a schematic block diagram illustrating example components of a social behaviors component.

FIG. 3 is a block diagram illustrating example components of the social behaviors component 212 of FIG. 2. In the depicted embodiment, the social behaviors component 212 includes a social path component 302, a classification component 304, a status determination component 306, an acknowledgment component 308, a gesture component 310, and a personality component 312. The components 302, 304, 306, 308, 310, and 312 are provided by way of example only and may not be included in all embodiments. For example, various embodiments may include any one or any combination of two or more of the components 302, 304, 306, 308, 310, and 312 without limitation.

The social path component 302 creates or modifies paths to maintain a socially acceptable distance from humans. In one embodiment, the social path component 302 creates paths based on the current status of the robot 100 or a detected person. In one embodiment, the current status includes the presence of a person. In one embodiment, the social path component 302 creates a path according to a first set of rules when a human is not present and creates a path according to a second set of rules when a human is present. In one embodiment, the first set of rules maximizes avoidance of collision with objects and the second set of rules maximizes collision avoidance with humans. For example, the first set of rules may cause the robot 100 to navigate down the middle of a navigable area, such as a hallway. This may maximize the distance between the robot and walls or objects near the walls. On the other hand, the second set of rules may cause the robot 100 to navigate down a side of the navigable area, such as to the left or the right of the center of the hallway when a human is detected. This may meet social expectations in the location of the robot 100. For example, in some cultures it is more common to stay to the right side of a pathway or hallway whereas in others it is more common to stay to the left side. The social path component 302 may cause the robot 100 to follow these customs when a person is detected.

Similarly, the distances between objects may vary between a set of rules for use when a human is not detected and a set of rules for use when a human is detected. For example, the social path component 302 may require that the robot 100 stay further away from objects when a human is not present than when a human is present. This may allow the robot 100 to provide a greater distance between the robot 100 and the human to help avoid collision with the human but also to allow the human to feel more comfortable. Similarly, a minimum distance between a human and the robot 100 may be greater than a minimum distance between an object and the robot 100.

The social path component 302 may be configured to cause the robot 100 to operate more efficiently and quickly when humans are not present than when humans are present. For example, the social path component 302 may allow for a greater top speed of the robot 100 as it travels a path without any humans around than when the humans are around. As another example, the social path component 302 may allow for a greater acceleration rate of the robot 100 as it travels a path without any humans around than when the humans are around.

The social path component 302 may be configured to cause the robot 100 to operate more predictably to a human when humans are present. This may allow for the human to be better able to predict the robot's path and thereby avoid the human bumping into the robot 100 or the robot 100 bumping into the human. Similarly, this may reduce the chance of the robot 100 getting closer to the human than the human would find comfortable. In one embodiment, the social path component 302 may cause the robot 100 to act more predictably to a human by reducing acceleration rates of the robot. These acceleration rates may include accelerations to speed up the robot 100, slow down the robot 100, or cause the robot 100 to change direction. Slower rates of acceleration may also be achieved by creating smoother and more rounded paths for the robot 100 to follow.

Figure 4:
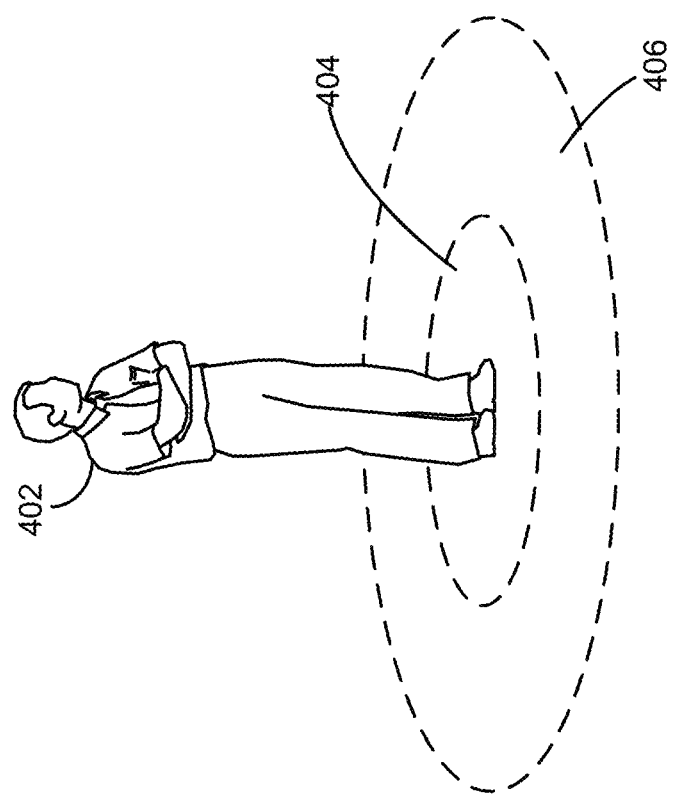
FIG. 4 is a perspective view illustrating a robot and a comfort zone and lockout zone around a human.
Figure 4:
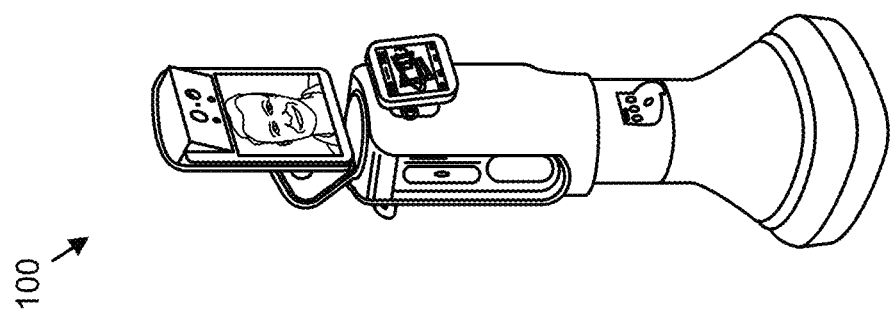

In one embodiment, the social path component 302 causes the robot 100 to reduce discomfort of nearby humans by observing a lockout zone and/or a comfort zone for each detected human. FIG. 4 illustrates a robot 100 and a nearby person 402. A lockout zone 404 and a comfort zone 406 for the human are illustrated. According to one embodiment, the social path component 302 may determine the size and shape of the lock out zone 404 and comfort zone 406. The social path component 302 may cause the robot 100 to avoid traveling through the lockout zone 404 and/or the comfort zone 406.

According to one embodiment, the lockout zone 404 defines an area through which the robot 100 may not pass. The social path component 302 may create or modify any path to avoid the lockout zone 404. The comfort zone 406 defines an area through which the robot 100 may pass, but must do so at a reduced maximum speed. In one embodiment, the social path component 302 may avoid passing through the comfort zone 406 as long as it is faster to pass around the comfort zone than slow down while passing through the comfort zone 406. By observing the lockout zone 404 and the comfort zone 406, the robot 100 may avoid making people feel uncomfortable by violating their personal space.

The lockout zone 404 and comfort zone 406 are given by way of illustration only. Similar lockout zones 404 and/or comfort zones 406 may also be used in relation to objects. The social path component's 302 path planning may allow for a relatively large lockout zone 404 or buffer space for people and a relatively small lockout zone 404 or buffer space for objects. For example, the radius of the lockout zone 404 for objects may be limited to between 0.5 and 12 inches; whereas, the radius of the lockout zone 404 for humans may be between 18 and 36 inches. This lockout zone 404 may be variable, depending on the cultural context the robot 100 is in, the amount of available space, the identity of the person, a classification of the person, a zone within a work area where the person 402 and the robot 100 are located, and/or the urgency with which the robot 100 is navigating. In some embodiments, the size of the buffer zone may be selected by a user and/or disabled by a user, such as a user who is remotely operating the robot 100. Based on the cultural context, if the robot 100 is deployed in a crowded city, it may use a 12-inch radius for a lockout zone 404 for a human. However, if the robot 100 is deployed in a less crowded city, the social path component 302 may use an 18-inch radius for a lockout zone 404.

Lockout or buffer zones may be adapted and specified for particular objects, situations, and/or locations. Merely by way of example and not limitation, the Table 1 represents possible lockout radii and comfort zones for various objects:

TABLE 1

| Detected Object | Lockout radius | Comfort zone |
|---|---|---|
| Bed | 12" | 18" |
| Chair | 8" | 12" |
| Cart on Wheels | 10" | 16" |
| Open drawer | 8" | 12" |
| Shelf, Countertop or Desk | 8" | 12" |
| Misc. medical equipment | 10" | 16" |
| Closed door | 12" | 18" |
| Gurney, stretcher | 12" | 18" |
| IV pole with bag | 10" | 16" |
| Wheelchair | 12" | 18" |

In various embodiments, the robot 100 may be configured to maintain socially acceptable distances for a wide variety of situations. Examples of managing natural social distances and other human-like behavior that may be performed by the robot 100 are described in U.S. patent application Ser. No. 11/541,422 titled "COMPANION ROBOT FOR PERSONAL INTERACTION," filed on Sep. 29, 2006, which application is hereby incorporated by reference in its entirety. For example, the robot 100 may be configured to make various gestural cues as the robot 100 moves or interacts with people.

In various embodiments, the robot 100 may act in a manner consistent with social protocols with regard to its speed. For example, the robot 100 may decelerate its traveling speed when it comes within a larger comfort zone 406 of a person 402. For example, if the lockout zone 404 has a radius of 18 inches, the larger comfort zone 406 may have a radius of 24-48 inches. The robot 100 may decelerate when it nears or enters this larger comfort zone 406. In one embodiment, the robot 100 may have a maximum speed of 5 mph with no humans around, and may decelerate to 2 mph when it enters the larger comfort zone 406. Accordingly, the robot 100 may travel at an average human walking speed within the environment of a heath care facility, taking into account the natural tendency of humans to slow down when in crowded situations or when close to other humans. For example, the robot 100 may determine an average walking speed of a detected individual and maintain the same average speed.

The classification component 304 may classify a detected person. For example, a classification component 304 of a robot 100 in a hospital may classify a detected person as one or more of a patient, a visitor, and a hospital worker. The classification component 304 may classify a person based on facial recognition, detection of a badge or wireless identification tag on the person, by location within a wheelchair or bed, by location in a work area, and/or by physical features. For example, the robot 100 may classify patients from other humans in the facility using a method such a SIFT-based identification to distinguish people located on a bed, gurney, or wheelchair.

Figure 5:
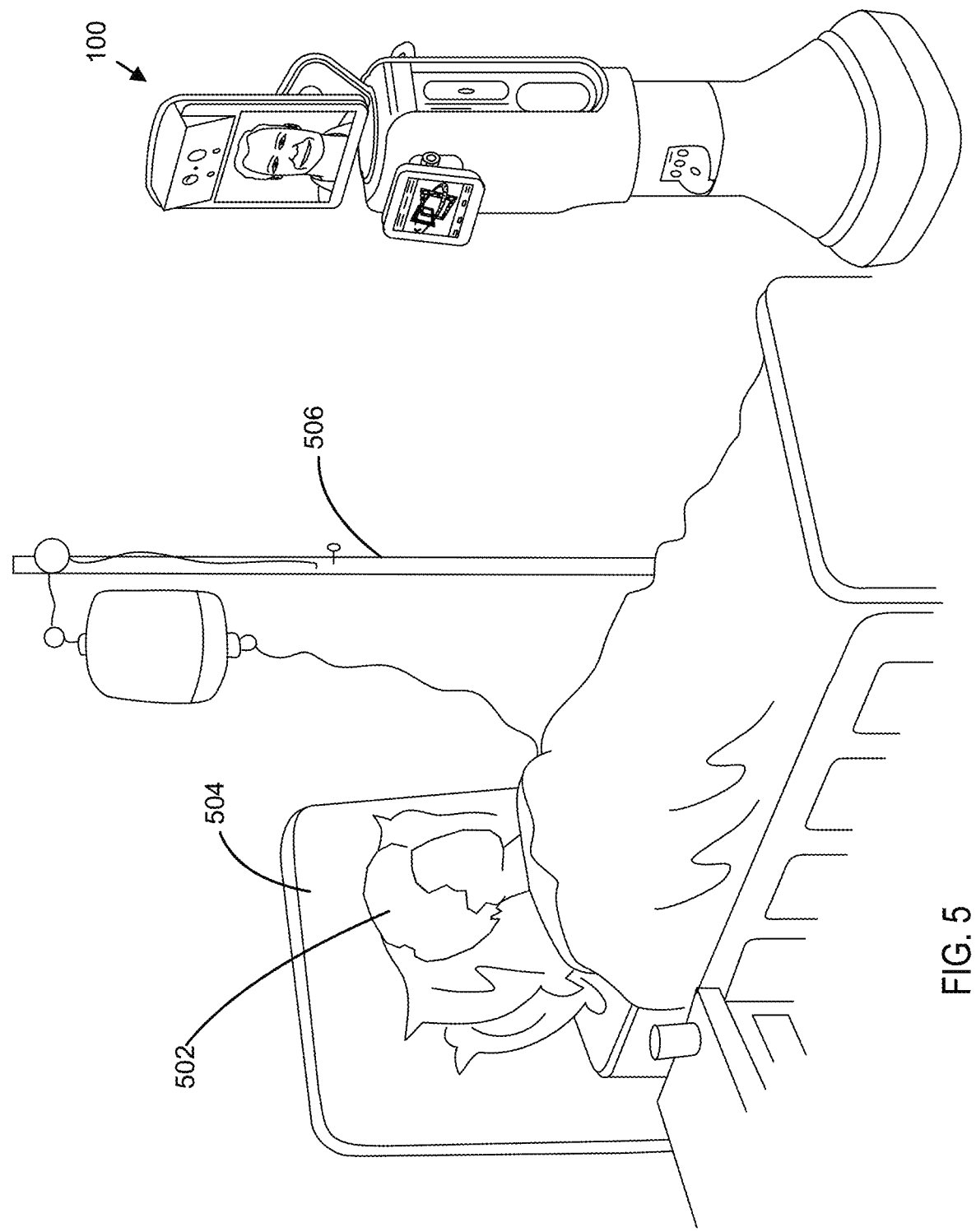
FIG. 5 is a perspective view of a robot near a patient in a bed.

FIG. 5 is a perspective view of a the robot 100 near a patient 502 in the patient's room. The patient 502 is shown within a hospital bed 504 and near an IV pole 506. In one embodiment, the classification component 304 may classify the patient 502 as a patient based on the patients location within the bed 504 and near the IV pole 506. The social path component 302 may cause the travel speed of the robot 100 to vary when it is in close proximity to a patient. In one embodiment, a patient room may act as a "patient zone," such that any person 402 in the room would be classified by the robot 100 as a patient. When the robot 100 detects a patient, it may increase the lockout zone 404 and comfort zone 406 radii from that of other people 402 in the hospital and/or adjust the speed limits for a given type of zone. In one embodiment, this ratio may be 1:1.5. Thus, for example, the lockout zone 404 radius may increase from 12 inches to 18 inches, and the comfort zone 406 radius may increase from 18 inches to 27 inches. This may serve to protect patient safety and/or patient emotional security, especially because patients may be in a sensitive emotional or physical state.

The social path component 302 may create a navigation path based on a classification of a nearby person. For example, when the robot 100 is near a patient or visitor in a hospital work area, the social path component 302 may afford greater distances to ensure that the visitor or patient is not disturbed. The social path component 302 may allow for a smaller lockout zone 404 or comfort zone 406 for hospital employees, such as doctors or nurses, than for visitors and patients.

The status determination component 306 determines a current status of the robot 100 or of a nearby person 402. For example, the status determination component 306 may determine whether there is an emergency, whether there is a human present, whether humans are engaged in a conversation, whether the robot 100 will navigate near an intersection, whether the robot 100 will navigate near a doorway, or other possible statuses of the robot 100 or a nearby person 402.

The status determination component 306 may determine that the current status includes nearby people involved in a conversation. The status determination component 306 may determine that two or more people are involved in a conversation and avoid passing between them. For example, the status determination component 306 may determine a conversation zone that includes a continuous region between the human and the one or more humans such that the telepresence robot cannot pass between the human and the one or more humans without passing through the conversation zone.

Figure 6:
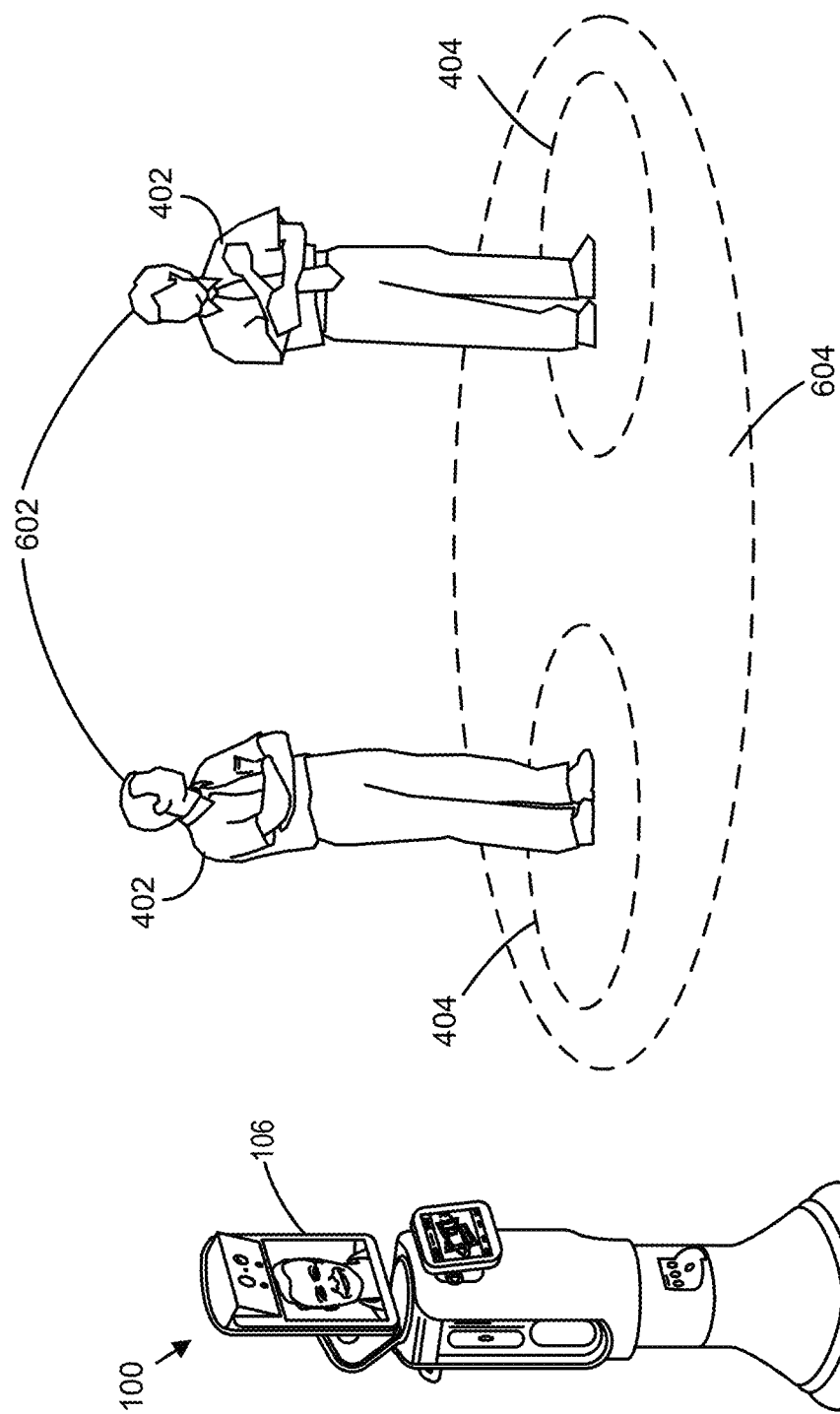
FIG. 6 is a perspective view illustrating a robot and a conversation zone and lockout zones around a group of humans.

FIG. 6 illustrates a robot 100 near two people 402 who are engaged in a conversation. The robot may recognize the people 402 as part of a conversational group 602 and avoid disturbing them by not moving in between the people 402. The robot 100 may be configured to plan its navigational path around clusters of humans, so as to avoid interrupting human interaction. The robot 100 may scan a room to detect humans clustered in groups 602 that may potentially be in conversation. In one embodiment, the robot 100 may scan a room to detect humans and then perform a segmentation and clustering analysis to detect potential conversational groups 602. From this analysis, the robot 100 may determine which direction the humans are facing, their proximity to other humans, hand gestures, or other actions indicating a group 602 of interacting humans. In other embodiments, the robot 100 may utilize sound detection techniques and/or analysis to identify humans that are potentially in a group 602. FIG. 6 illustrates a conversation zone 604 and respective lockout zones 404 for each person 402. The social path component 302 may avoid the conversation zone 604 similar to how it avoids a comfort zone 406. Alternatively, when human groups 602 are detected, the robot 100 may apply a lockout zone 404 and/or comfort zone 406 to the entire group 602, as opposed to individual humans within the group 602. Accordingly, the robot 100 may avoid interrupting conversations between humans in a group 602 and may treat the conversation zone 604 similar to a lockout zone.

Similarly, the status determination component 306 may determine other groups of people and/or objects that the robot 100 should not pass between. In addition to attempting to abide by social protocols when navigating around humans, the robot 100 may also adhere to specific behavioral protocols when navigating around specific objects common to healthcare facilities. In some embodiments, the robot 100 may have special, pre-determined lockout radii and/or comfort zones for each respective object. Other objects may trigger special-case behaviors. For example, when the robot 100 finds a cable or cord, it may determine whether to traverse or avoid the cable depending on the cable's height. In other embodiments, the robot 100 may alter its behavior based on alerts or existing conditions. For example, the robot 100 may alter its behavior based on a "floor cleaning" sign. In such an example, the robot 100 may respond by slowing its speed to 50% and staying within a few inches of a wall. Another example may include the robot 100 detecting a patient with an IV pole or walker, which may cause the robot 100 to avoid navigating between the patient and the IV pole or walker.

Figure 7:
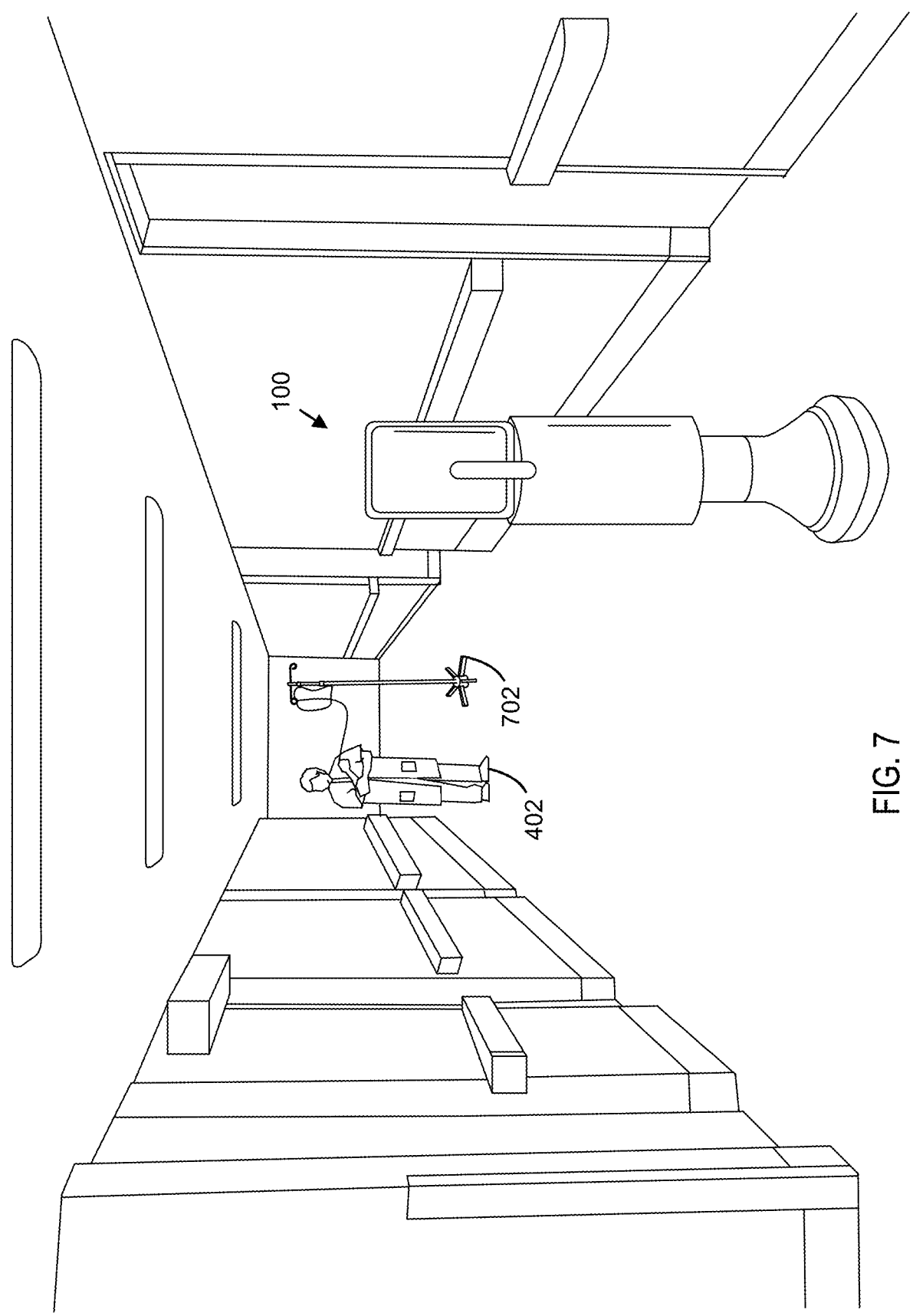
FIG. 7 is a perspective view of a robot approaching a patient and intravenous pole in a hallway.

FIG. 7 illustrates a perspective view of the robot 100 approaching a person 402 and an IV pole 702 in a hallway. According to one embodiment, the object detection system 206 detects the person 402 and IV pole 702 and the status determination component 306 determines that the robot 100 should not pass between a person 402 and an IV pole 702 based on a stored rule. For example, even though the robot 100 may not be able to see tubing running between the person 402 and the IV pole 702 the robot may follow a rule that the robot 100 should not pass between them. Thus, the social path component 302 may plan a path around the person 402 and IV pole 702 that does not involve passing between them.

The status determination component 306 may determine that the current status includes that the robot 100 is approaching a doorway or intersection. The status determination component 306 may determine that the robot 100 is approaching a doorway or intersection based on information detected by the object detection system 206 and/or based on a current location of the robot 100 as determined by the map component 210. The status determination component 306 may notify the social path component 302 of the upcoming doorway or intersection and the social path component 302 may determine a path to pass through the doorway or intersection while limiting chances of entering a lockout zone 404 of any people 402 or bumping into any objects or people. For example, the social path component 302 may determine an entry angle through the intersection or doorway to increase visibility to any approaching humans. Similarly, as the robot 100 approaches the doorway or intersection, the status determination component 306 and/or the social path component 302 may determine whether a human will reach the intersection within a threshold time of the robot 100. If the human and the robot 100 will likely cross around the same time the social path component 302 may modify a path of the robot 100 to avoid a lockout zone 404 for the human. The social path component 302 may change the path such that the robot 100 stops at the intersection, speeds up, slows down, or even moves sideways to avoid coming within a lockout zone 404 and/or comfort zone 406 of the human.

The social path component 302 may also avoid sudden, unexpected changes in direction or movements that might potentially surprise or disturb a human.

Figure 8:
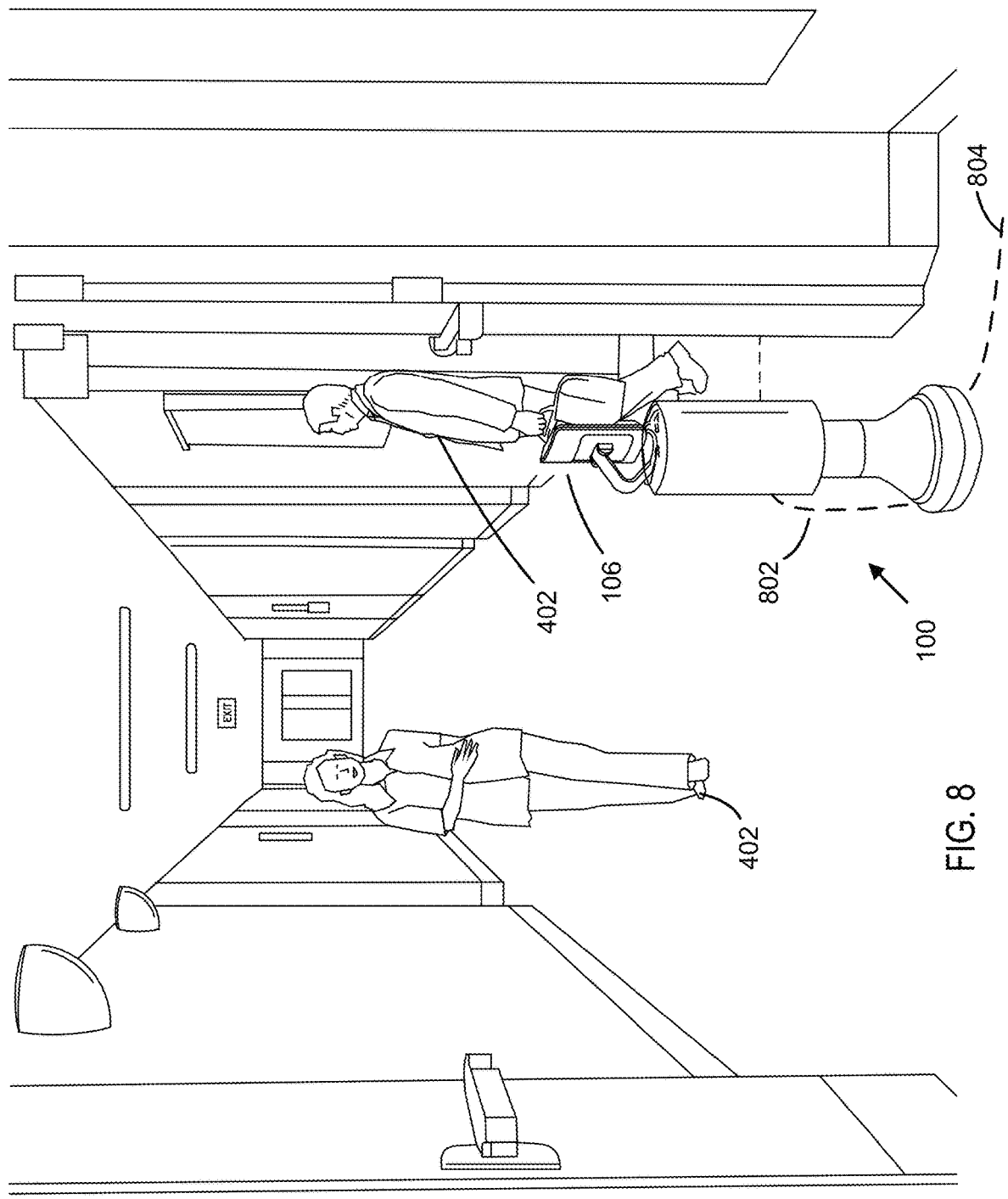
FIG. 8 is a perspective view of a robot approaching an intersection.

FIG. 8 illustrates a perspective view of a robot 100 as the robot 100 navigates around a corner at an intersection. The robot 100 is shown approaching the intersection while two people 402 are also passing through the intersection. A planned pathway 802 is shown around the corner of the intersection that will be predictable for the people 402. For example, the pathway 802 is a smooth rounded pathway and sweeps wide around the corner to increase visibility for the robot 100 and any more people that may be coming. The social path component 302 may determine that the robot 100 will be the first to get around the corner and may thus proceed. In one embodiment, the robot 100 may determine that the people 402 will be in the intersection about the same time as the robot 100 and the social path component 302 may determine that it would be best for the robot to stop until the people 402 are through the intersection. In one embodiment, the robot 100 may determine that it has a right of way since it is turning to the right and may proceed around the corner even if the people 402 might need to wait.

With respect to thresholds in doorways or intersections, the status determination component 306 may be configured to cause the robot 100 to slow down, approach thresholds at an angle, and/or approach the threshold squarely. In some embodiments, the robot 100 may have an omnidirectional drive system 202 configured to move in any direction, regardless of the orientation or angle of the base 102 relative to the motion. However, in some embodiments an omnidirectional base may be configured to climb or traverse a raised threshold or other object better at one angle than another. Accordingly, the status determination component 306 may be configured to orient its base 102 at the optimal angle relative to a threshold prior to traversing the threshold. For example, a three- or four-wheel base 102 may traverse a raised threshold better if it is oriented squarely with respect to the threshold, such that two wheels of the base 102 contact the raised threshold at the same time. In some embodiments, thresholds may be included in a map of the healthcare facility. For example, raised thresholds for doorways may be tagged or otherwise marked on a map used by the robot 100 for navigation. In some embodiments, the thresholds may be detected by the robot 100 as it approaches them.

The status determination component 306 may determine that the current status includes that the robot 100 is being delayed during navigation. The status determination component 306 may determine that the robot 100 is being delayed during navigation when a pathway is blocked by one or more individuals and objects for at least a delay time period. The robot 100 may encounter obstacles that prevent it from passing, such as a person 402, a group 602 of people, an object, or a combination thereof. The robot 100 may attempt to plan a navigational path to avoid breaching social rules for a specified timeout period, after which it may attempt to find a new route to its destination and/or violate the social rules. In some embodiments, the timeout period may be short, such as between 1 and 30 seconds, to avoid the robot 100 hovering or dodging around people in the hallway for a long period of time while they are talking or otherwise engaged in the hallways. In still other embodiments, the robot may ask people to step aside or move.

Returning to FIG. 7, the social path component 302 may determine that it cannot maneuver down the hallway without entering a lockout zone 404 of the person 402 or IV pole 702. Upon determining the path is blocked the status determination component 306 may start a timer and continue looking for a way around the person 402 and IV pole 702. If the timer reaches a delay time the status determination component 306 may determine that the robot 100 is in a delayed navigation status. The social path component 302 may, in response, shrink a lockout zone 404 of the person 402 or IV pole 702 and then attempt to find a route through. If a path is found the social path component 302 may cause the robot 100 to continue on its path. Otherwise, the social path component 302 may seek for a new pathway.

Similarly, when located in narrow, crowded, or otherwise tight spaces, the robot 100 may leave a small buffer of space between itself and an object, but may pass relatively close to objects in order to navigate.

The status determination component 306 may determine that the current status includes that a nearby human is involved in an emergency. The status determination component 306 may determine that a nearby human is involved in an emergency based on how fast a nearby human is moving. For example, if the object detection system 206 detects that a human is moving at a fast pace down a hallway, the status determination component 306 may determine that the user is involved in an emergency or has an urgent task to perform. Similarly, the status determination component 306 may determine that a nearby person is involved in an emergency based on one or more of a speed of a moving object, a speed of a moving person, a warning sound, and flashing lights. In another embodiment, the robot 100 may detect the velocity of the approaching person or object and, if it is above a pre-determined threshold, determine that there is an emergency or dangerous situation. In this case, the robot 100 may move to the side of the hallway and wait until the passing person, group, and/or object has passed.

In one embodiment, upon determination that a person is involved in an emergency, the social path component 302 may determine a path to cause the robot 100 to move out of a high-traffic area, move out of the way of the person or object involved in an emergency, or the like. Returning to FIG. 8, the robot 100 is shown approaching an intersection. According to one embodiment, if one or both of the people 402 were moving at a faster rate than is normal for people in the work area, the robot 100 may stop and follow the other path 804, instead of the planned path 802, to get out of the way for a short amount of time or until the intersection or hallway has cleared. Similarly, the social path component 302 may determine that another location is more ideal for getting out of the way and may cause the robot 100 to navigate to the other location.

The robot may be configured to detect or receive an indication of the urgency of the approaching object. For example, the speed of an approaching gurney may be indicative of the urgency of the situation. In another embodiment, a gurney may have a transmitter or lights that indicate the urgency of the situation. The robot 100 may respond by moving out of the way. The robot 100 may also be prohibited from loitering in high-traffic areas. For example, hallways may be marked as areas where the robot 100 should not stop, or in which the robot 100 should move to one side of the hallway if it does stop.

The robot 100 may be more sensitive to emergencies in an emergency department (ED) region. For example, the robot 100 may be more likely to stop and wait at the side when people move by. For example, the robot 100 may utilize the motion and velocity detection behaviors described above, but adjust them for the ED region, such that a velocity of 50% of the normal emergency velocity threshold may be enough to trigger an emergency response behavior of waiting by a wall for the fast-moving person or object to pass. Similarly, the robot 100 may increase its lockout zones 404 and/or comfort zones 406 for objects in an ED unit to decrease the likelihood that it will collide with a shelf or table containing delicate instruments.

The status determination component 306 may determine that the current status includes that the robot 100 is involved in an emergency or has an urgent status. For example, while being remotely operated by a doctor, the doctor may select an option for urgent operation of the robot 100. In one embodiment, in response to receiving an indication that the robot 100 is involved in an emergency situation, the robot 100 may be configured to violate one or more of the social protocols discussed herein. For example, the robot 100 may violate the group conversation rule to reach a high-priority destination by traveling between two humans having a conversation. In another embodiment, the robot 100 may need to reduce the size of a lockout zone by a predetermined fraction, such as one half. Similarly, increased speed or other changes in restrictions may be followed. In addition, the robot 100 may be configured to play a sound clip of a polite phrase, such as, "excuse me" or "I'm sorry."

The status determination component 306 may determine the current status as being located within a specific region of a work area. In one embodiment, the robot 100 may have the ability to change its navigational settings depending on the different areas of the hospital through which it is traveling. In some embodiments, the map component 210 may allow the robot 100 to determine which region of the hospital it is in, and the robot 100 may adapt its operation accordingly. For example, the robot 100 may adjust behaviors, such as how far it navigates into a room, the speeds it travels, the radii of the lockout zone 404 and/or buffers between itself and objects, and other behaviors. In some embodiments, the robot 100 in an intensive care unit (ICU) region or a pediatric ward may adjust its maximum speed to 50% of its normal pace. In another embodiment, the robot 100 may navigate only a specified distance into an ICU room from the doorway. For example, the robot 100 may move only far enough into a room to view information from monitors. In this example, the rest of the room may be considered a lockout zone 404.

The social path component 302 may also allow the robot 100 to exhibit team based behavior. In one embodiment, for example, the display interface 108 on the upper portion 104 of the robot 100 may present a "follow team" option that may be selected by a user. When the follow team option is selected, the robot 100 may identify various features of a person to be followed, such as height, facial features, size, or other physical characteristics. The social path component 302 may then follow the identified individual at a predetermined distance. The robot 100 may accomplish this using the object detection system 206 that performs methods such as facial detection and/or other detection and following techniques. When following an individual, the robot's 100 speed and lockout zones may be adjusted to comply with a team-based environment. In some embodiments, the robot's 100 lockout zone may be reduced to allow it closer physical proximity to the team or followed individual, and/or the comfort zone may be reduced or eliminated entirely. In other embodiments, the speed of the robot 100 may be adjusted to match a time-averaged speed of the team or individual.

The social path component 302 may also exhibit team behavior by getting out of the way of an oncoming person. For example, the social path component 302 may cause the robot 100 to move in a human-like way in response to objects or people moving in its direction, even if they have not crossed into its navigational path. In one embodiment, the robot 100 may respond to a human presence in a hallway by moving closer to one side of the hallway, decelerating as the person or object approaches, moving to the side of the hallway and stopping until the person or object has passed, and/or by performing other human-like reactions. In one embodiment, if the robot determines that a hallway is narrow, the robot 100 may decelerate as a person and/or object approach. The robot 100 may stop next to the wall as a person and/or object approach in a narrow hallway, and resume once they have passed. In one embodiment, the robot 100 may use any of the various detection methods described above, such as a motion detection method, to choose the side of the hallway opposite of the detected movement (or choose either side of the hallway if the motion is from the center of the hallway, or the side of the hallway that is less congested with other obstacles). In one embodiment, the robot 100 may be configured to always go toward either the right or the left, based on a user specification. In another embodiment, the robot 100 may detect if the hallway is narrow and decelerate accordingly.

Figure 9A:
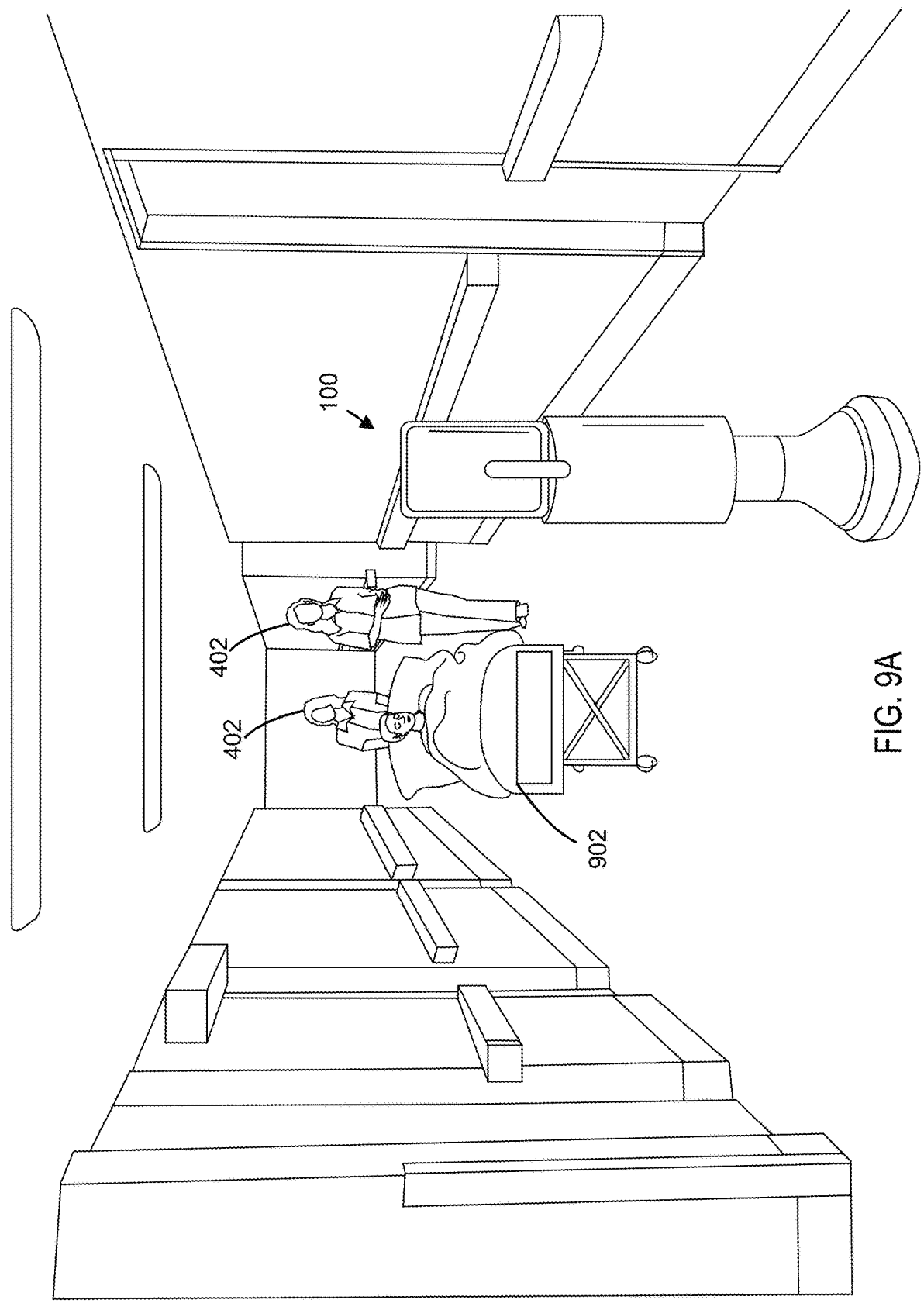
FIG. 9A is a perspective view of a robot approaching large group in a hallway.

FIGS. 9A and 9B are perspective views of the robot 100 in a hallway with some people 402 and a patient in a bed 902 approaching. According to one embodiment, the robot 100 recognizes in FIG. 9A that the people 402 and the patient in the bed 902 take up most of the hallway and are moving toward the robot 100. The social path component 302 may determine that the robot 100 should move over and let the people 402 and the patient in the bed 902 pass. In FIG. 9B, the robot 100 has followed a path 904 to a side of the hallway and stopped to let the people 402 and the patient in the bed 902 pass. The robot 100 may then proceed on its way once the group has passed.

The acknowledgment component 308 may be configured to provide acknowledgement or other visible information to nearby humans. For example, the acknowledgment component 308 may be configured to cause the robot 100 to socially acknowledge a human, indicate a direction to be traveled by the robot, indicate a state or status of the robot 100, apologize for violating a social rule, or the like. The acknowledgment component 308 may provide the acknowledgement or indications visually, audibly, or using a gesture.

The acknowledgment component 308 may provide acknowledgment or other indications using the lights 114. For example, the acknowledgment component 308 may us the lights 114 or other lights located on the base 102, upper portion 104, head, front, back, and/or other areas to indicate direction, intended direction, urgency, or usage, and/or to set a mood. In one embodiment, if a pathway is blocked by a human the acknowledgment component 308 may flash the lights 114 to get the attention of a person blocking the path. Various colors of lights 114 may be associated with moods and/or contexts. For example, blue may be calming or soothing, while red or yellow may indicate an emergency. The lights may also indicate if a robot 100 is being tele-operated or is autonomously navigating.

In one embodiment, the acknowledgment component 308 flashes the lights 114 to indicate that the robot 100 is in an emergency or urgent status. Similarly, flashing lights may indicate that the robot 100 is delayed. For example, in the scenarios discussed above, the acknowledgment component 308 may turn on the lights 114, flash the lights 114, or the like to indicate that the robot 100 may act in a more urgent manner and may pass closer and/or move more quickly than normal. For example, the robot 100 may use the lights 114 as a blinker to indicate that the robot 100 will turn to the right. Nearby people will notice the flashing lights 114 and pay attention or move out of the way of the robot 100.

The acknowledgment component 308 may provide acknowledgment or other indications by making an audible sound, such as by using a speaker. For example, the acknowledgment component 308 may also provide an audible warning, or apology, to nearby humans when it violates a comfort zone, reduced lockout zone, conversation zone, or the like. For example, the robot 100 may play an audio clip that says "I'm sorry," "excuse me," or the like. As another example, the robot 100 may play a subdued siren sound, beeping sound, or other warning sound when the robot 100 is in an urgent mode or when it has been delayed. This may provide a notification to nearby individuals that the robot 100 is there and may be trying to get by. In one embodiment, the acknowledgment component 308 causes the robot 100 to provide a social acknowledgment to a passing human. For example, the robot 100 may say "hello" or provide any other audible greeting to a passing human.

When the robot 100 needs to violate any rules, it may apologize to the humans by playing the sound clip as it passes. The robot 100 may also issue a warning before it violates a social rule. For example, a warning may be issued by playing a sound clip of a pre-recorded polite phrase. In other embodiments, this warning may be issued by flashing lights 114 on the upper portion 104 of the robot 100.

The acknowledgement component 308 may also cause a gesture component 310 to perform a gesture to indicate a status or acknowledge a passing human. For example, gestures may be performed to indicate a direction to be traveled, acknowledge the human, or the like.

The gesture component 310 may be configured to perform a gesture to indicate a direction to be traveled. For example, the gesture component 310 may cause the head 106 of the robot 100 to turn in the direction the robot 100 intends to travel. The head 106 may be turned prior to the robot 100 actually moving in that direction. This is similar to how humans often turn their head in the direction they intend to walk before moving in that direction. Humans can generally read this body language and know where a person intends to walk and can thus avoid walking in the same direction, slowing to let that person pass, or the like. Similarly, by turning its head 106 in the direction it intends to travel the robot 100 may naturally communicate a direction to be traveled to nearby humans where the robot 100 will go. This may reduce the likelihood of the robot 100 coming within a lockout zone 404 or comfort zone 406 of the person 402. This is partly because the movement is rendered more predictable to the human because of the gesture.

Similar gestures may also be performed at doorways or near other blind spots. The robot 100 may utilize a navigational algorithm that causes the robot 100 to face the direction of its motion. For instance, rather than facing forward and panning to the left or right, the robot 100 may turn its body portion and/or head portion in the direction of the movement. The robot 100 may also imitate human behavior by rotating its head portion to the left and right (scan) over a room or corridor before entering. If the head portion of the robot 100 faces a different direction than the actual movement, humans in the surrounding region may find it unnatural, disturbing, distracting, and/or otherwise be made to feel uncomfortable. Accordingly, the robot 100 may imitate human behavior by maintaining its head portion facing the direction of movement, other than for brief periods as described herein (e.g., when greeting).

In one embodiment, the robot 100 may decelerate its approach to a threshold, stop to scan the room or intersection, and then adjust its navigational path if necessary. In other embodiments, the robot 100 may not come to a complete stop, but may decelerate to a very slow speed such as between 0.1 mph and 2 mph as it scans the room or intersection.

FIG. 8 illustrates an example of a head turn gesture to indicate a direction. The robot 100 is shown turning its head 106 to the right even though the robot 100 has yet to begin moving to the right, as indicated by the path 802. In addition to gesturing, the robot 100 may provide other indications to allow hospital staff and visitors to know where the robot 100 is headed. These indicators may include the robot's head 106 facing the direction of its motion (as discussed above), or having the robot 100 turn its head 106 to "look" to the side it intends to turn when it approaches an intersection. Other indicators may include lights 114, such as light emitting diodes (LEDs), on the robot 100 that act as turn indicators. The lights 114 may be visible from the front or rear. The indicators on the appropriate side may turn on or flash a pre-determined distance from the robot's 100 turn.

The gesture component 310 may be configured to perform a gesture to acknowledge a passing person 402. The robot 100 may use a method, such as motion detection, facial recognition techniques, or other detection methods to detect humans. In one embodiment, the robot 100 may turn its head 106 to face the human briefly, and then return to face the direction of its travel. In other embodiments, the robot 100 may keep its face pointed toward the human's face for a moment, so as to simulate the equivalent of human eye contact. In other embodiments, the robot 100 may be configured to simulate a nod to the human, such as by tilting its head 106 downward, then returning its head 106 to face its forward direction. The robot 100 may also be configured to greet humans in the hallway by playing a pre-recorded sound clip of a greeting such as, "hello" or "good morning."

FIG. 9B also illustrates the head turn gesture to acknowledge the people 402. The robot 100 has moved to the side of the hallway and turned its head 106 to "look" at the passing group. The robot 100 may pan the head 106 to face the group for a short period of time to simulate eye contact. In one embodiment, the robot 100 may only pan the head 106 toward the people 402 for only a short time so that the people 402 do not feel like they are being stared down. The robot 100 may also nod the head 106 by tilting the head 106 forward and then back up. The robot 100 may also play an audible greeting.

Figure 9C:
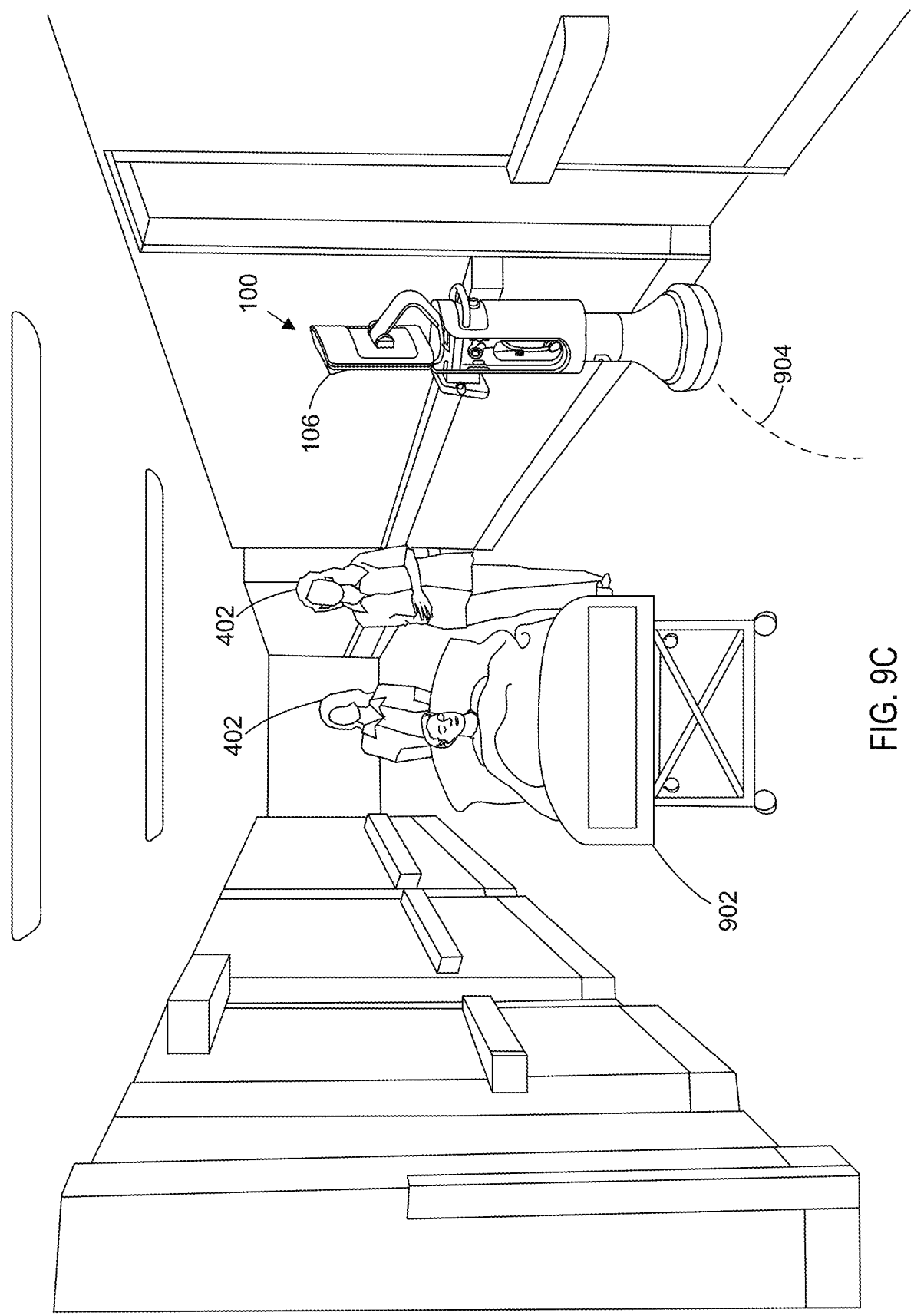
FIG. 9C is a perspective view of a robot allowing the large group of FIG. 9A to pass with a body portion rotated

FIG. 9C illustrates an alternative embodiment in which the body of the robot 100 (along with the head 106) has rotated to "look" at the passing group. Again, the robot 100 may also nod the head 106 by tilting the head 106 forward and then back up. The robot may be configured to turn only the head 106, as illustrated in FIG. 9B, or it may be configured to rotate the body as well, as illustrated in FIG. 9C.

Throughout this disclosure, the concept of a robot "turning its head" may include a robot turning a head portion relative to a body portion. Alternatively, "turning its head" may include a robot with a fixed head, and thus require that the robot rotate more than just a head portion (e.g., the upper portion 104, a base 102, or even the complete robot) in order to "turn its head" and "look" in a particular direction or at a particular object.

The personality component 312 may control the robot 100 to operate according to an assigned personality. For example, a personality may be assigned to the robot to cause it to behave in certain ways. For example, a shy robot may only nod, while an outgoing robot may greet each human verbally as it passes. Similarly, the types of acknowledgments may vary between different personality types. The personality component 312 may also cause the lights 114 to light up according to the personality type and may display a caricature corresponding to the personality type. For example, caricatures that may amuse children may be used in a children's section of a hospital.

Returning to FIG. 2, the biohazard detection component 214 is configured to detect a potential biohazard. The biohazard detection component 214 may detect the presence of a potential biohazard and/or identify a type of biohazard. For example, the biohazard detection system may include one or more sensors that detect the presence of a potential biohazard. In one embodiment, the biohazard detection component 214 includes a sensor that grazes a floor of a work area as the robot 100 moves through a work area. In one embodiment, the senor may include a moisture sensor. For example, the moisture sensor may detect spilled chemicals, blood, urine, or other fluids that may be potential biohazards. In one embodiment, the sensor may include a chemical sensor that detects the presence of one or more chemicals. For example, some chemicals may be present in different biohazard materials. The chemical sensor may allow the biohazard detection component 214 to detect the chemical and determine that a biohazard or potential biohazard is present.

In one embodiment, the biohazard detection component 214 may detect a potential biohazard by detecting material on a floor of a work area that is not part of the floor based on an image captured by a camera of the robot 100. For example, the biohazard detection component 214 may perform image analysis to detect liquid, powders, or other materials on a floor of the work area. The biohazard detection component 214 may be capable of identifying a material based on color, location, size, shape, texture, etc. Similarly, a moisture sensor or chemical sensor may also be used to identify a type of biohazard or potential biohazard.

The biohazard safety component 216 is configured to provide instructions to the control system to cause the robot 100 to prevent spreading of a detected potential biohazard. The biohazard safety component 216 may prevent spreading of the potential biohazard by stopping on or near the potential biohazard to block others from walking through the potential biohazard and spreading it throughout a work area. The biohazard safety component 216 may provide a warning to nearby humans about the detected potential biohazard. In one embodiment, the biohazard safety component 216 may cause the robot 100 to flash a biohazard symbol on the display interface 108. In one embodiment, the biohazard safety component 216 may cause the robot 100 to flash one or more lights 114 to indicate an emergency or urgent situation. In one embodiment, an audible warning may be played by the robot 100 that indicates that there is a potential biohazard and instructing humans to avoid it. In one embodiment, a biohazard symbol, flashing lights, and an audible warning may all be provided.

The biohazard safety component 216 may prevent spreading of the potential biohazard by transmitting a message that there is a detected potential biohazard. For example, the biohazard safety component 216 may cause the communication system 208 to send a message over a wireless network to indicate the location, type of potential biohazard, and/or other information about the potential biohazard. A cleaning crew or other management crew may receive the message and be able to address the problem and/or clean up the biohazard.

The biohazard safety component 216 may prevent spreading of the potential biohazard by cleaning up the biohazard. The biohazard safety component 216 may be equipped with cleaning tools to clean up a liquid, powder, or any other material. The biohazard safety component 216 may include a sterilization pad and/or drying pad to sterilize and/or dry the area where the potential biohazard was detected. Thus, the robot 100 may be capable of maintaining sanitation in a work area, such as a hospital. The robot 100 may send a message that the potential biohazard was cleaned and one or more workers may be able to double check whether there is any more cleaning that needs to be done.

Figure 10:
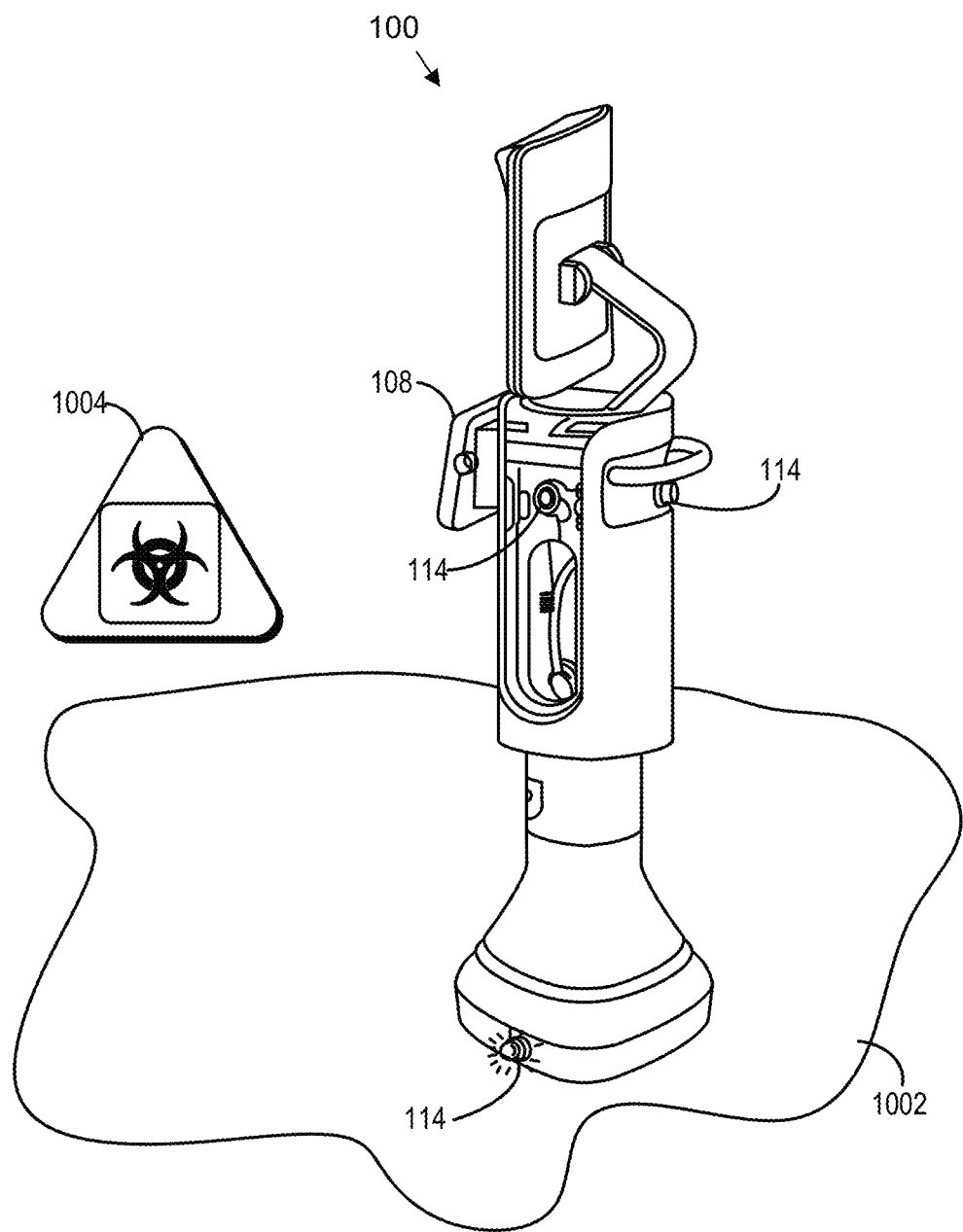
FIG. 10 is a perspective view illustrating a robot in a potential biohazard.

FIG. 10 illustrates a robot 100 that has detected a potential biohazard 1002. According to one embodiment, the robot 100 automatically halts movement upon detection of the biohazard 1002. The robot 100 may be exposed to biohazards 1002 in the form of liquids on the hospital floor such as blood, urine, or other fluids. To avoid spreading such a contamination throughout the healthcare facility, the robot 100 may be equipped with a sensor to detect a liquid or chemical. In one embodiment, this sensor may be a lightweight, flexible sensor that protrudes from the base 102 of the robot 100, and grazes the floor. In another embodiment, the robot 100 may have a chemical sensor that extends from the robot 100 and detects or confirms the detection of the biohazard 1002. The sensor may include a moisture sensor. In yet another embodiment, the robot may employ computer vision, image analysis, or scene analysis techniques to identify a spill, puddle, or other object or substance that is not a part of the floor. In this case the robot 100 may send an alert or notification to the appropriate personnel but navigate around the hazard and continue its current mission.

When the biohazard detection component 214 detects a biohazard, the robot 100 may stop immediately. After the robot 100 stops, it may turn on a signal to alert healthcare facility staff. In another embodiment, the display interface 108 may flash a "Biohazard Detected" message with a biohazard symbol 1004. This message may also be present with options that the healthcare facility staff could select such as, "Resume," "Shut Down," and "Wait." In another embodiment, the robot 100 may send a short message service (SMS) message (or other electronic message) to hospital maintenance or to the manufacturer's tech support department to alert them of the biohazard 1002. In another embodiment, the healthcare facility and/or the robot 100 may be equipped with sterilization pads. The robot 100 may utilize a sterilization pad to perform an auto clean to destroy the biohazard 1002 and sterilize the area. In some embodiments, the sterilization pad may be placed adjacent to a re-lubrication pad, in case the sterilization effort removes the robot 100 wheel lubrication. In other embodiments, a drying pad may also be utilized.

Some of the components that can be used with embodiments disclosed herein are already available, such as general-purpose computers, mobile phones, computer programming tools and techniques, digital storage media, and communications networks. A computing device, such as a laptop, tablet computer, desktop computer, server, Smartphone, or the like, may include a processor, such as a microprocessor, microcontroller, logic circuitry, or the like. The processor may include a special purpose processing device such as an ASIC, PAL, PLA, PLD, FPGA, or other customized or programmable device. The computing device may also include a computer-readable storage device such as non-volatile memory, static RAM, dynamic RAM, ROM, CD-ROM, disk, tape, magnetic, optical, flash memory, or other computer-readable storage medium.

Various aspects of certain embodiments may be implemented using hardware, software, firmware, or a combination thereof. As used herein, a software component may include any type of computer instruction or computer executable code located within or on a non-transitory computer-readable storage medium. A software component may, for instance, comprise one or more physical or logical blocks of computer instructions, which may be organized as a routine, program, object, component, data structure, etc., which performs one or more tasks or implements particular abstract data types.

In certain embodiments, a particular software component may comprise disparate instructions stored in different locations of a computer-readable storage medium, which together implement the described functionality of the component. Indeed, a component may comprise a single instruction or many instructions, and may be distributed over several different code segments, among different programs, and across several computer-readable storage media. Some embodiments may be practiced in a distributed computing environment where tasks are performed by a remote processing device linked through a communications network.

The systems and methods disclosed herein are not inherently related to any particular computer or other apparatus and may be implemented by a suitable combination of hardware, software, and/or firmware. Software implementations may include one or more computer programs comprising executable code/instructions that, when executed by a processor, may cause the processor to perform a method defined at least in part by the executable instructions. The computer program can be written in any form of programming language, including compiled or interpreted languages, and can be deployed in any form, including as a standalone program or as a module, component, subroutine, or other unit suitable for use in a computing environment. Further, a computer program can be deployed to be executed on one computer or on multiple computers at one site or distributed across multiple sites and interconnected by a communication network.

Software embodiments may be implemented as a computer program product that comprises a non-transitory storage medium configured to store computer programs and instructions that, when executed by a processor, are configured to cause the processor to perform a method according to the instructions. In certain embodiments, the non-transitory storage medium may take any form capable of storing processor-readable instructions on a non-transitory storage medium. A non-transitory storage medium may be embodied by a compact disk, digital-video disk, a magnetic tape, a Bernoulli drive, a magnetic disk, a punch card, flash memory, integrated circuits, or any other non-transitory digital processing apparatus memory device.

Although the foregoing has been described in some detail for purposes of clarity, it will be apparent that certain changes and modifications may be made without departing from the principles thereof. It should be noted that there are many alternative ways of implementing the processes, apparatuses, and system described herein. Accordingly, the present embodiments are to be considered illustrative and not restrictive, and the invention is not to be limited to the details given herein, but may be modified within the scope and equivalents of the appended claims.

As used herein, the terms "comprises," "comprising," and any other variation thereof, are intended to cover a non-exclusive inclusion, such that a process, a method, a system, an article, or an apparatus that comprises a list of elements does not include only those elements but may include other elements not expressly listed or inherent to such process, method, system, article, or apparatus.

It will be obvious to those having skill in the art that many changes may be made to the details of the above-described embodiments without departing from the underlying principles of the invention. The scope of the present invention should, therefore, be determined only by the following claims.

What is claimed is:

1. A telepresence robot comprising:
a drive system configured to move the telepresence robot;
a control system configured to control the drive system to drive the telepresence robot around a work area;
an object detection system configured to determine whether an object encountered by the telepresence robot is a human;
a social behaviors component configured to provide instructions to the control system to cause the telepresence robot to maintain a first distance from the object if the object is a human and a second distance from the object if the object is not a human; and
a status determination system to determine a current status for the telepresence robot, the current status including a location of the telepresence robot, wherein the second distance is greater when the telepresence robot is in a first location than when the telepresence robot is in a second location.

2. The telepresence robot of claim 1, wherein the second distance comprises a predetermined minimum distance.

3. The telepresence robot of claim 1, wherein the social behaviors component determines the second distance from the human based on a zone where the human and the telepresence robot are located.

4. The telepresence robot of claim 1, wherein the second distance for an intensive care unit zone of a hospital is greater than the second distance for another zone of the hospital.

5. The telepresence robot of claim 1, wherein the current status comprises an emergency status for the human.

6. The telepresence robot of claim 1, wherein the current status comprises an emergency status for the telepresence robot.

7. The telepresence robot of claim 1, wherein the status determination system determines the current status based on a speed at which the human is moving.

8. The telepresence robot of claim 1, wherein the first distance is used for maximizing avoidance of collision with objects, and wherein the second distance is used for avoiding collisions with humans.

9. The telepresence robot of claim 1, wherein the social behaviors component is further configured to instruct the control system to cause the telepresence robot to operate according to a first set of rules when a presence of one or more humans is not detected and operate according to a second set of rules when the presence of one or more humans is detected.

10. The telepresence robot of claim 9, wherein the first set of rules comprises navigating in a middle of a navigable area when a presence of one or more humans is not detected.

11. The telepresence robot of claim 9, wherein the second set of rules comprises navigating toward a side of a navigable area when the presence of one or more humans is detected.

12. The telepresence robot of claim 9, wherein the first set of rules comprises traveling at a first maximum speed and wherein the second set of rules comprises traveling at a second maximum speed, wherein the second maximum speed is less than the first maximum speed.

13. The telepresence robot of claim 1, wherein the object detection system is configured to detect the human using a camera.

14. The telepresence robot of claim 13, wherein the object detection system is configured to detect the human using one or more of face detection, feature classification for body shapes, and motion detection.

15. A telepresence robot comprising:
a drive system configured to move the telepresence robot;
a control system configured to control the drive system to drive the telepresence robot around a work area;
an object detection system configured to determine whether an object encountered by the telepresence robot is a human; and
a social behaviors component configured to provide instructions to the control system to cause the telepresence robot to maintain a first distance from the object if the object is a human and a second distance from the object if the object is not a human, wherein the second distance for an intensive care unit zone of a hospital is greater than the second distance for another zone of the hospital.

* * * * *